US012612358B2

(12) United States Patent
McAllister et al.

(10) Patent No.: US 12,612,358 B2
(45) Date of Patent: Apr. 28, 2026

(54) RESORCINOL-BASED COMPOUNDS AND USES THEREOF

(71) Applicants: Sutter Bay Hospitals, San Francisco, CA (US); Organix, Inc., Woburn, MA (US)

(72) Inventors: Sean D. McAllister, Milbrae, CA (US); Pierre-Yves Desprez, Richmond, CA (US); Anuradha Mahadevan, Westford, MA (US); Ravi K. Ujjinamatada, Lexington, MA (US)

(73) Assignees: Sutter Bay Hospitals, San Francisco, CA (US); Organix Inc., Woburn, MA (US)

( * ) Notice: Subject to any disclaimer, the term of this patent is extended or adjusted under 35 U.S.C. 154(b) by 395 days.

(21) Appl. No.: 18/266,771

(22) PCT Filed: Dec. 16, 2021

(86) PCT No.: PCT/US2021/063747

§ 371 (c)(1),
(2) Date: Jun. 12, 2023

(87) PCT Pub. No.: WO2022/133058

PCT Pub. Date: Jun. 23, 2022

(65) Prior Publication Data

US 2024/0059646 A1 Feb. 22, 2024

Related U.S. Application Data

(60) Provisional application No. 63/126,800, filed on Dec. 17, 2020.

(51) Int. Cl.

| | |
|---|---|
| ***C07C 235/64*** | (2006.01) |
| ***A61K 31/513*** | (2006.01) |
| ***A61P 35/04*** | (2006.01) |

(52) U.S. Cl.
CPC .......... *C07C 235/64* (2013.01); *A61K 31/513* (2013.01); *A61P 35/04* (2018.01)

(58) Field of Classification Search
CPC ... C07C 235/64; C07C 2601/14; C07C 65/05; C07C 65/105; C07C 65/21; C07C 65/24; C07C 235/62; A61K 31/513; A61K 31/337; A61K 45/06; A61P 35/04; C07D 213/75; C07D 239/42; C07D 295/135; C07D 295/155
See application file for complete search history.

(56) References Cited

U.S. PATENT DOCUMENTS

| | | | |
|---|---|---|---|
| 9,771,345 | B2 | 9/2017 | Barany et al. |
| 2002/0161041 | A1 | 10/2002 | Browning et al. |

OTHER PUBLICATIONS

PubChem ID 130456532 (Year: 2017).*
Chatel, Cecile, International Preliminary Report on Patentability and Written Opinion, PCT/US2021/063747, The International Bureau of WIPO, Jun. 29, 2023.
Pubmed Compound Record for CID 130456532, '4-(2,2-dimethylpropyl)-2,6-dihydroxybenzamide,' U.S. National Library of Medicine, Oct. 7, 2017, pp. 1-8 (https:/pubchem.ncbi.nlm.nih.gov/compound/130456532).
Pubmed Compound Record for CID 130286492, '4-tert-butyl-2,3,5,6-tetrahydroxybenzoic acid,' U.S. National Library of Medicine, Oct. 7, 2017, pp. 1-8 (https://pubchem.ncbi.nlm.nih.gov/compound/130286492).
Rodriquez, Kari, International Search Report and Written Opinion, PCT/US2021/063747, United States Patent & Trademark Office, May 13, 2022.

* cited by examiner

*Primary Examiner* — Kamal A Saeed
*Assistant Examiner* — Meghan C Heasley
(74) *Attorney, Agent, or Firm* — Gavrilovich, Dodd & Lindsey LLP

(57) ABSTRACT

The disclosure provides for resorcinol-based compounds, pharmaceutical compositions made therefrom, and methods of treatment thereof for various disorders, including neoplastic disorders.

19 Claims, 3 Drawing Sheets

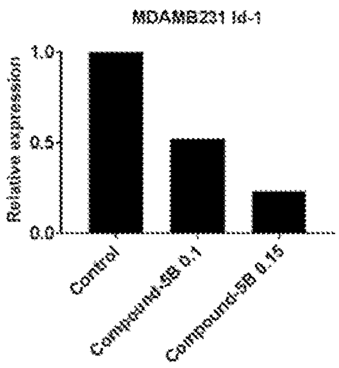
FIG. 1A
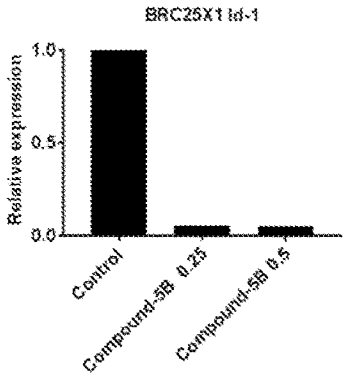
FIG. 1B
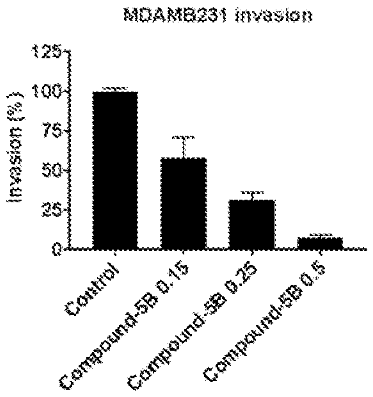
FIG. 1C
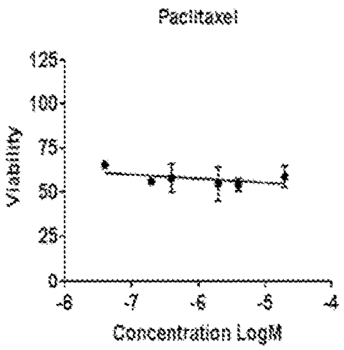
FIG. 2A
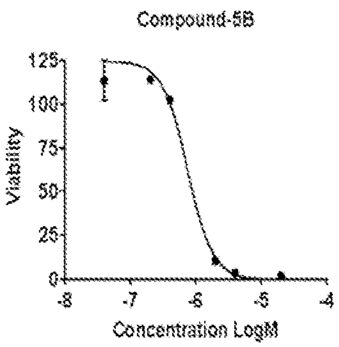
FIG. 2B
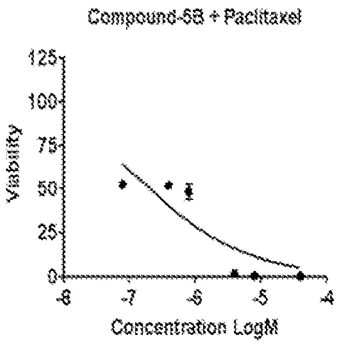
FIG. 2C
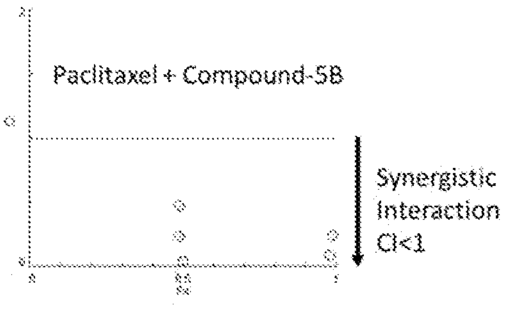
FIG. 3A
| Dose Paclitaxel (μM) | Dose Compound-5B (μM) | Fraction affect (Fa)/Effect on Cell Proliferation | CI |
|---|---|---|---|
| 0.002 | 0.002 | 0.5 | 0.04 |
| 0.01 | 0.01 | 0.49 | 0.23 |
| 0.02 | 0.02 | 0.49 | 0.47 |
| 0.05 | 0.05 | 0.98 | 0.09 |
| 0.2 | 0.2 | 0.99 | 0.24 |
FIG. 3B

RESORCINOL-BASED COMPOUNDS AND USES THEREOF

CROSS REFERENCE TO RELATED APPLICATIONS

This application is a U.S. National Phase application filed under 35 U.S.C. § 371 and claims priority to International Application No. PCT/US2021/063747, filed Dec. 16, 2021, which application claims priority to U.S. Provisional Application Ser. No. 63/126,800, filed on Dec. 17, 2020, the disclosures of which are incorporated herein by reference.

STATEMENT REGARDING FEDERALLY SPONSORED RESEARCH

This invention was funded by Grant Nos. CA102412, CA171415, CA20672 and CA111723 awarded by the National Institutes of Health. The government has certain rights in the invention.

TECHNICAL FIELD

The disclosure provides for resorcinol-based compounds, pharmaceutical compositions made therefrom, and methods of treatment for various disorders thereof, including neoplastic disorders.

BACKGROUND

The inhibitor of DNA binding (Id) proteins are helix-loop-helix transcriptional repressors with established roles in stem cell self-renewal, lineage commitment, and niche interactions. While deregulated expression of Id proteins in cancer was identified more than a decade ago, emerging evidence has revealed a central role for Id proteins in neoplastic progression of multiple tumor types that often mirrors their function in physiological stem and progenitor cells. Id proteins are required for the maintenance of cancer stem cells, self-renewal, and proliferation in a range of malignancies, including pancreatic cancer, breast cancer, prostate cancer, non-small cell lung cancer, gastric cancer, melanoma, glioblastoma, hepatocarcinoma, and anaplastic thyroid tumor. Furthermore, Id proteins promote metastatic dissemination through their role in remodeling the tumor microenvironment and by promoting tumor-associated endothelial progenitor cell proliferation and mobilization.

SUMMARY

The disclosure provides for resorcinol-based compounds that exhibited significant biological activity and pharmacokinetic properties for treating cancer (e.g., pancreatic cancer). The resorcinol-based compounds of the disclosure, like Compound-5B, demonstrated significant activity at targeting Id-1 expression and pancreatic cancer aggressiveness in culture. For example, in a subcutaneous xenograft model of human pancreatic cancer, Compound-5B was found to be as efficacious as gemcitabine, with a significantly improved toxicity profile.

In a particular embodiment, the disclosure provides for a resorcinol-based compound having the structure of Formula I:

(I)

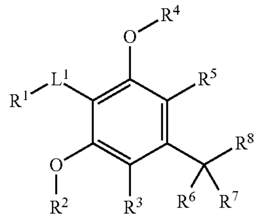

or a pharmaceutically acceptable salt, or prodrug thereof, wherein:

$L^1$ is selected from,

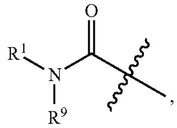
,
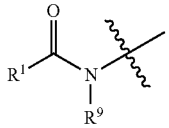
,
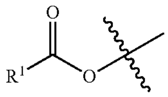
, and
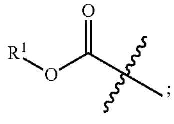
;

$R^1$ is selected from H, —OH, an optionally substituted $(C_5\text{-}C_{12})$cycloalkyl, an optionally substituted $(C_5\text{-}C_{12})$cycloalkenyl, an optionally substituted $(C_5\text{-}C_{12})$cycloalkynyl, an optionally substituted aryl, an optionally substituted heterocycle, and an optionally substituted extended mixed ring system; $R^2$, $R^4$, $R^6$, and $R^7$ are each independently selected from H or a $(C_1\text{-}C_3)$alkyl; $R^3$ and $R^5$ are each independently selected from H, hydroxyl, a $(C_1\text{-}C_3)$alkyl, and a halo; $R^8$ is selected from an optionally substituted $(C_1\text{-}C_{12})$alkyl, an optionally substituted $(C_1\text{-}C_{11})$ hetero-alkyl, an optionally substituted $(C_1\text{-}C_{12})$ alkenyl, an optionally substituted $(C_1\text{-}C_{11})$ hetero-alkenyl, an optionally substituted $(C_1\text{-}C_{12})$alkynyl, an optionally substituted $(C_1\text{-}C_{11})$ hetero-alkynyl, an optionally substituted aryl, an optionally substituted $(C_3\text{-}C_{12})$cycloalkyl, an optionally substituted $(C_3\text{-}C_{12})$cycloalkenyl, and an optionally substituted heterocycle; and $R^9$ is selected from H, and a $(C_1\text{-}C_3)$alkyl. In another embodiment, the disclosure provides for a resorcinol-based compound has a structure of Formula I(a):

I(a)

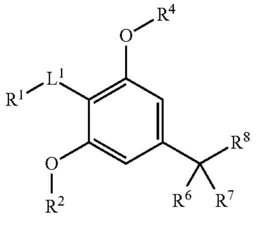

or a pharmaceutically acceptable salt, or prodrug thereof, wherein:

$L^1$ is selected from,

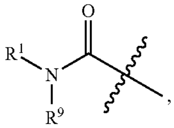, and 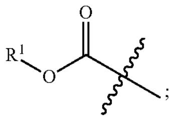;

$R^1$ is selected from H,

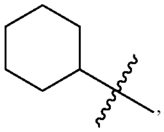, 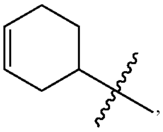, 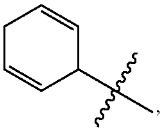,

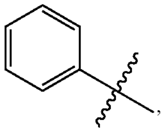, 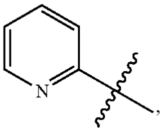, 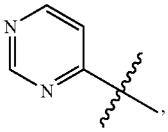,

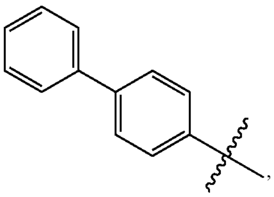, 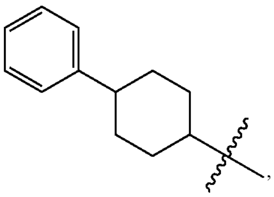,

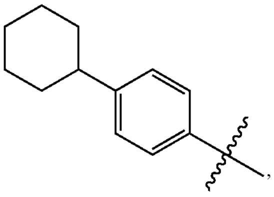, 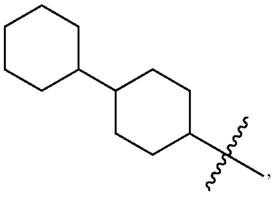,

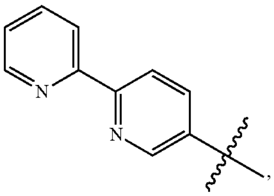,

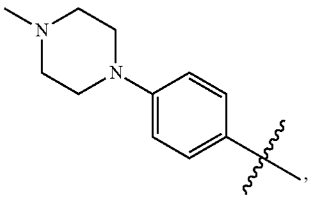,

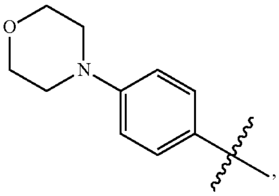, 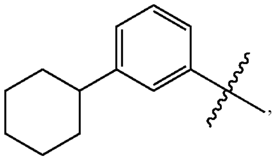,

-continued

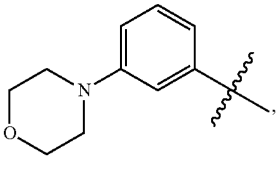,

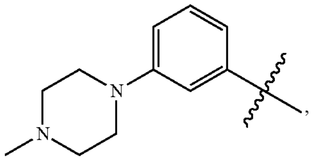, 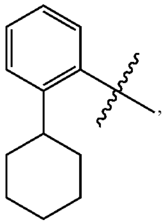,

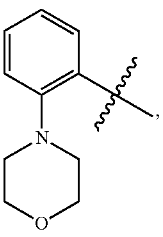, and 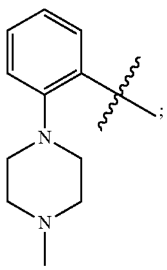;

$R^2$, $R^4$, $R^6$, and $R^7$ are each independently selected from H or a methyl group; $R^8$ is selected from an optionally substituted $(C_1-C_{12})$alkyl, an optionally substituted $(C_1-C_{11})$ hetero-alkyl, an optionally substituted $(C_1-C_{12})$alkenyl, an optionally substituted $(C_1-C_{11})$ hetero-alkenyl, an optionally substituted $(C_1-C_{12})$alkynyl, an optionally substituted $(C_1-C_{11})$ hetero-alkynyl, an optionally substituted aryl, an optionally substituted $(C_3-C_{12})$cycloalkyl, an optionally substituted $(C_3-C_{12})$cycloalkenyl, and an optionally substituted heterocycle; and $R^9$ is selected from H, and a $(C_1-C_3)$alkyl. In yet a further embodiment, the disclosure also provides for a resorcinol-based compound that has a structure of Formula I(b):

I(b)

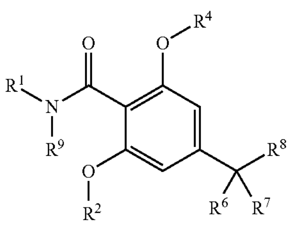

or a pharmaceutically acceptable salt, or prodrug thereof, wherein:

$R^1$ is selected from H,

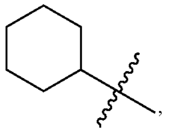, 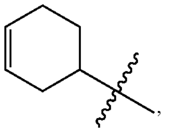, 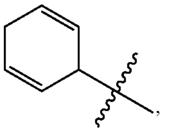,

-continued

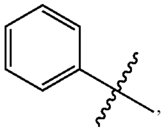,
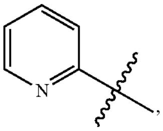,
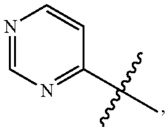,

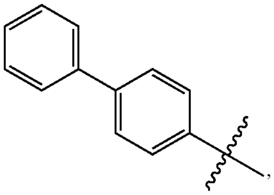,
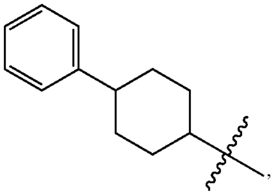,

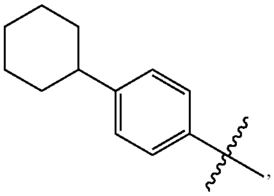,
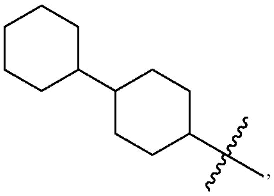,

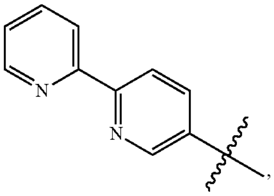,

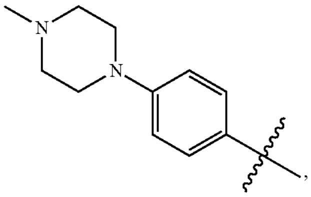,

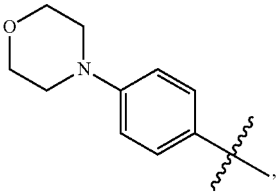,
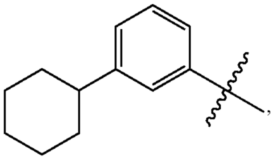,

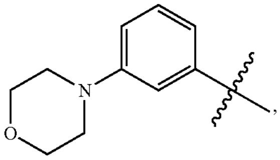,

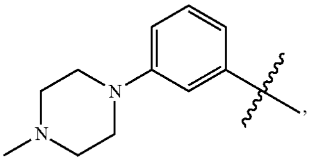,
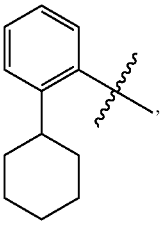,

-continued

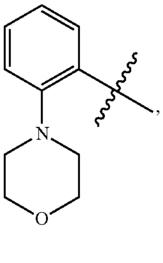, and
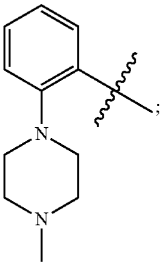;

$R^2$, $R^4$, $R^6$, and $R^7$ are each independently selected from H or a methyl group;

$R^8$ is selected from a ($C_1$-$C_{12}$) alkyl, a ($C_2$-$C_{12}$) alkenyl, a ($C_2$-$C_{12}$)alkynyl, a ($C_3$-$C_8$)cycloalkyl, an aryl, a heterocycle, a —$(CH_2)_x$-aryl, a —$(CH_2)_x$-cycloalkyl, and a —$(CH_2)_x$-heterocycle, wherein X is an integer selected from 1, 2, 3, 4, 5, 6, 7, 8, 9, and 10; and $R^9$ is selected from H, and a ($C_1$-$C_3$)alkyl. In a yet another embodiment, the disclosure also provides for a resorcinol-based compound which has a structure selected from the group consisting of:

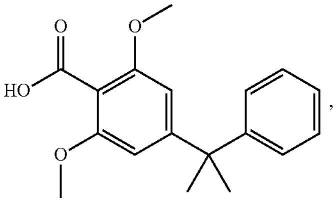,

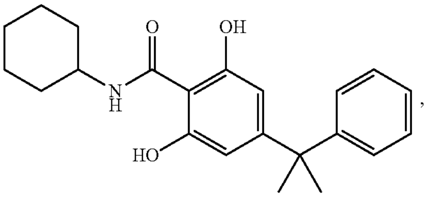,

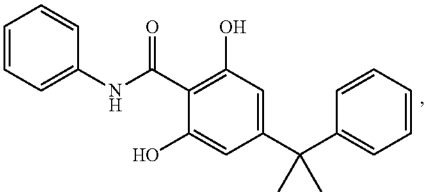,

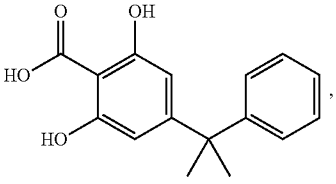,

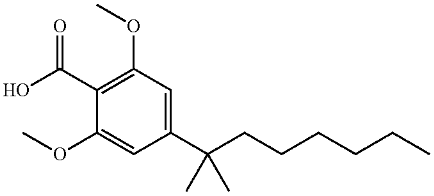,

-continued

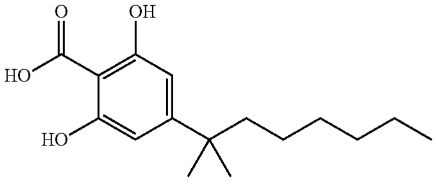,

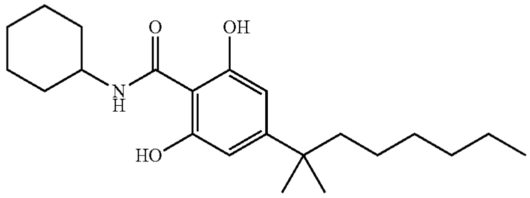,

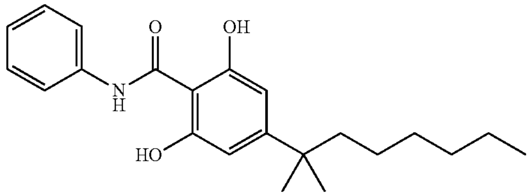,

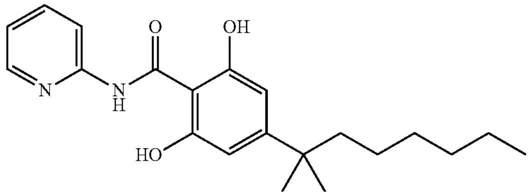,

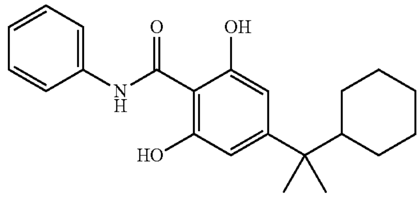,

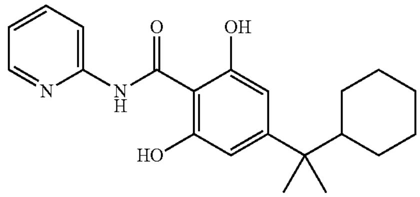,

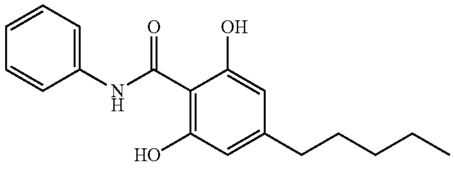,

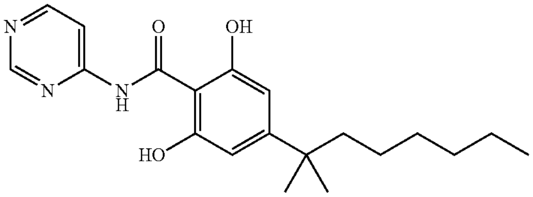,

-continued

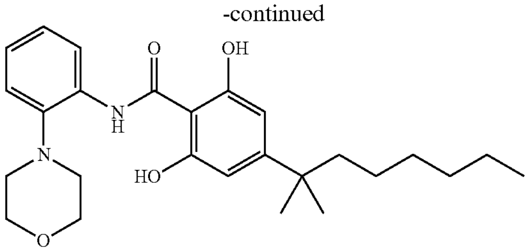,

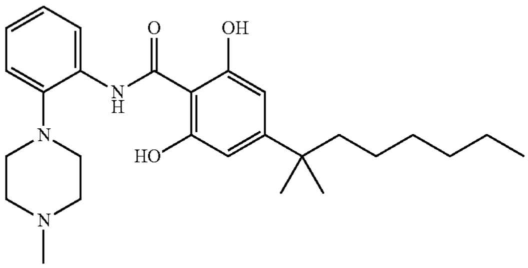,

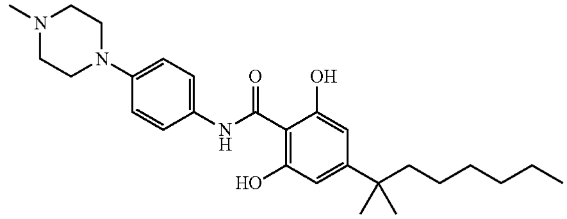

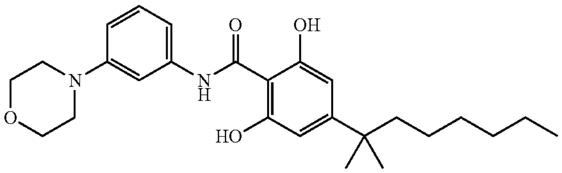,

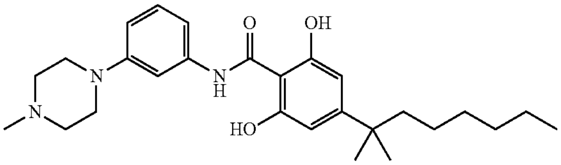,

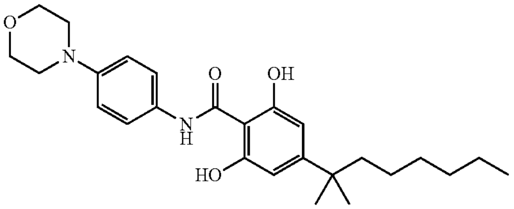, and

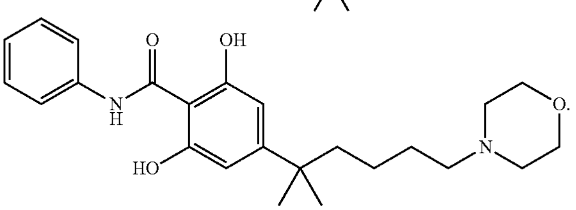

In a certain embodiment, the disclosure provides for a pharmaceutical composition comprising a resorcinol-based compound disclosed herein and a pharmaceutically acceptable diluent, carrier and/or excipient. In a further embodiment, the pharmaceutical composition is formulated for oral or parenteral delivery. In yet a further embodiment, the pharmaceutical composition further comprises one or more additional therapeutic agents. In another embodiment, the one or more additional therapeutic agents is selected from the group consisting of alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, and chemotherapeutic agents. In yet another embodiment, the additional therapeutic agent is gemcitabine or 5-FU.

In a certain embodiment, the disclosure further provides a method for regulating the expression of an inhibitor of DNA binding (Id), comprising contacting a cell that expresses the Id with an effective amount of a resorcinol-based compound disclosed herein. In yet a further embodiment, the Id is Id-1.

In a particular embodiment, the disclosure also provides a method for treating a cancer in a subject in need thereof, comprising: administering to the subject an effective amount of a resorcinol-based compound disclosed herein, or a pharmaceutical composition of the disclosure. In a further embodiment, the cancer is a metastatic cancer. In another embodiment, the cancer is selected from the group consisting of pancreatic cancer, breast cancer, prostate cancer, non-small cell lung cancer, gastric cancer, melanoma, glioblastoma, hepatocarcinoma, and anaplastic thyroid tumor. In yet another embodiment, the cancer is pancreatic cancer.

In a certain embodiment, the disclosure provides a method for inhibiting cancer cell invasiveness and metastatic progression in a subject in need thereof, comprising: administering to the subject an effective amount of a resorcinol-based compound disclosed herein, or a pharmaceutical composition of the disclosure. In a further embodiment, the cancer cell invasiveness and metastatic progression is inhibited by downregulating Id-1 expression. In yet a further embodiment, the subject has a cancer selected from the group consisting of pancreatic cancer, breast cancer, prostate cancer, non-small cell lung cancer, gastric cancer, melanoma, glioblastoma, hepatocarcinoma, and anaplastic thyroid tumor. In a particular embodiment, the subject has pancreatic cancer.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 1A-C Compound-5B has significant potency for inhibition of Id-1 expression in MDA-MB231 cells (FIG. 1A) and primary patient-derived BRC25 cells (FIG. 1B). It also inhibits the invasion of MDA-MB231 cells (FIG. 1C).

FIG. 2A-C presents data showing the effects of Compound-5B (FIG. 2A) and paclitaxel (FIG. 2B) on breast cancer cell viability alone and in combination (FIG. 2C).

FIG. 3A-B demonstrates that at optimal combined ratios, Compound-5B can enhance the ability of paclitaxel to inhibit the viability of MDA-MB231 breast cancer cells. Concentration-response curves were generated for Compound-5B and paclitaxel alone and in combination (FIG. 2C). The inhibitory values from the concentration response curves were used to calculate combination index (CI) values at multiple combination ratios (FIG. 3A). Multiple viability assays in a 384-well format were run for each compound and the average percent inhibition of cell viability was calculated and transformed to fraction affected (Fa) e.g., percent inhibitory effect. CI values were calculated using Compusyn software (FIG. 3B), where CI<1, =1, and >1 indicate synergism, additive effect, and antagonism, respectively.

FIG. 4B and FIG. 4C demonstrate that Compound-5B inhibits breast cancer metastasis and primary tumor growth in mouse models of TNBC.

DETAILED DESCRIPTION

Figure 4A:
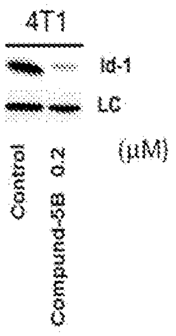
FIG. 4A-C shows Compound-5B produced downregulation of Id-1 protein expression. LC=loading control (FIG. 4A).

As used herein and in the appended claims, the singular forms "a," "an," and "the" include plural referents unless the context clearly dictates otherwise. Thus, for example, reference to "a resorcinol-based compound" includes a plurality of such resorcinol-based compounds and reference to "the cancer" includes reference to one or more cancers, and so forth.

Also, the use of "or" means "and/or" unless stated otherwise. Similarly, "comprise," "comprises," "comprising," "include," "includes," "including," "have," "haves," and "having" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

For purposes of this disclosure, the term "alkyl" refers to an alkyl group that contains 1 to 30 carbon atoms. Where if the alkyl group contains more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

For purposes of this disclosure, the term "alkenyl" refers to an alkenyl group that contains 2 to 30 carbon atoms. An alkenyl group of three or more carbons can contain more than one double covalent bond. In certain instances, the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkenyl may be substituted or unsubstituted, unless stated otherwise.

For purposes of this disclosure, the term "alkynyl" refers to an alkynyl group that contains 2 to 30 carbon atoms. An alkynyl group of three or more carbons can contain more than one triple covalent bond. Where if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkynyl may be substituted or unsubstituted, unless stated otherwise.

For purposes of this disclosure, the term "cylcoalkyl" refers to an alkyl that contains at least 3 carbon atoms but no more than 12 carbon atoms connected so that it forms a ring. A "cycloalkyl" for the purposes of this disclosure encompasses from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof. A "cycloalkyl group" can include bicyclic and tricyclic alkyl groups.

For purposes of this disclosure, the term "aryl" refers to a conjugated planar ring system with delocalized pi electron clouds that contain only carbon as ring atoms. An "aryl" for the purposes of this disclosure encompasses from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof. More specifically, substituted aryl groups include acetyl phenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

For purposes of this disclosure, the term "heterocycle" refers to ring structures that contain at least 1 noncarbon ring atom. A "heterocycle," as used herein, encompasses from 1 to 7 heterocycle rings wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

For purposes of this disclosure, the terms "heterocyclic group", "heterocyclic moiety", "heterocyclic", or "heterocyclo" used alone or as a suffix or prefix, refer to a heterocycle that has had one or more hydrogens removed therefrom.

For purposes of this disclosure, the term "hetero-" when used as a prefix, such as, hetero-alkyl, hetero-alkenyl, hetero-alkynyl, or hetero-hydrocarbon, refers to the specified hydrocarbon group having one or more carbon atoms replaced by one or more non carbon atoms. Examples of such non carbon atoms include, but are not limited to, N, O, S, Si, Al, B, and P. If there is more than one non carbon atom in the hetero-chain then this atom may be the same element or may be a combination of different elements, such as N and O.

For purposes of this disclosure, the term "extended mixed ring system" refers to a group that is comprised of at least 2 ring structures, but no more than 7 ring structures. An "extended mixed ring system" is comprised of at least one ring functional group that is different from another ring functional group. Examples of ring groups include, but are not limited to, cycloalkyl, cycloalkenyl, cycloalkynyl, aryl, and heterocycle. Each ring may be optionally substituted. The rings comprising the mixed extended ring system may be joined so that they are linked, fused, or a combination thereof.

For purposes of this disclosure, the term "unsubstituted" with respect to hydrocarbons, heterocycles, and the like, refers to structures wherein the specified group contains no substituents.

For purposes of this disclosure, the term "substituted" or "substitutions" with respect to hydrocarbons, heterocycles, and the like, refers to structures wherein the specified group contains one or more substituents.

For purposes of this disclosure, the term "substituent" refers to an atom or group of atoms substituted in place of a hydrogen atom. For purposes of this disclosure, a substituent would include deuterium atoms. Examples of "substituents" include, but are not limited to the following: alkyls, alkenyls, alkynyls, aryls, hetero-alkyls, hetero-alkenyls, hetero-alkynyls, cycloalkyls, cycloalkenyls, cycloalkynyls, heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, silyls, and $Si(OH)_3$.

For purposes of this disclosure, the term "functional group" or "FG" refers to specific groups of atoms attached to a parent chain or located within a parent chain that are responsible for the characteristic chemical reaction of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Larger functional groups, such as hydrocarbons, esters, and heterocycles, can be optionally substituted. Examples of FG that are used in this disclosure include, but are not limited to, alkyls, alkenyls, alkynyls, aryls, hetero-alkyls, hetero-alkenyls, hetero-alkynyls, cycloalkyls, cycloalkenyls, cycloalkynyls, heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, silyls, and $Si(OH)_3$.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

As used herein, a bond indicated by a straight line and a dashed line indicates a bond that may be a single covalent bond or alternatively a double covalent bond.

For purposes of the disclosure the term "cancer" will be used to encompass cell proliferative disorders, neoplasms, precancerous cell disorders and cancers, unless specifically delineated otherwise. Thus, a "cancer" refers to any cell that undergoes aberrant cell proliferation that can lead to metastasis or tumor growth. Exemplary cancers include but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, Merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, soft tissue sarcoma, uterine cancer, uterine sarcoma, skin cancer (non-melanoma), skin cancer (melanoma), papillomas, actinic keratosis and keratoacanthomas, Merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In a particular embodiment, the cancer is selected from the group consisting of melanoma, colorectal cancer, pancreatic cancer, bladder cancer, breast cancer, triple negative breast cancer, ovarian cancer and lung cancer.

The term "pharmaceutically acceptable" as in pharmaceutically acceptable salt or pharmaceutically acceptable counter ion, refers to compounds, salts, or ions that are tolerated by a subject for topical, or internal use.

The term "pharmaceutically acceptable salt" refers to making a salt formation of a compound disclosed herein. Salt formation can be used as a means of varying the properties of the compounds disclosed herein, for example, to increase or decrease solubility of the compounds, to improve stability of the compounds, to reduce toxicity of the compounds, and/or to reduce the hygroscopicity of the compounds. There are a wide range of chemically diverse acids and bases, with a range of pKa values, molecular weights, solubilities and other properties, that can used for making pharmaceutically acceptable salts of the compounds disclosed herein. Examples of pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure can form pharmaceutically acceptable salts with various amino acids. Examples of pharmaceutically acceptable base addition salts include, but are not limited to, aluminum, calcium, lithium, magnesium, potassium, sodium, zinc, and diethanolamine salts. For additional examples of pharmaceutical salts that can used to practice this disclosure, see P. H. Stahl and C. G. Wermuth (eds.), *Pharmaceutical Salts: Properties, Selection, and Use* (2d ed. 2011) Wiley and Sons Publisher, ISBN: 978-3-90639-051-2.

The term "pharmaceutically acceptable counter ion" either refers to pharmaceutically acceptable cations including, but not limited to, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyls, i.e., including, methyl, ethyl, or hydroxyethyl, specifically, trimethyl ammonium, triethyl ammonium, and triethanol ammonium cations); or pharmaceutically-acceptable anions including, but not limited to, halides (e.g., $Cl^-$, $Br^-$), sulfate, acetates (e.g., acetate, trifluoroacetate), ascorbates, aspartates, benzoates, citrates, and lactate.

The term "metastasis" generally refers to a multi-step process by which aggressive cancer cells spread out of the primary tissue and into other tissues of the body. Aggressive cancer cells that are nourished through angiogenesis, can migrate out of the primary tissue, and invade into the blood stream. These migratory aggressive cancer cells can remain vital by escaping the immune response, and consequently evade the blood stream and invade other tissues of the body. These cells can then proliferate to create secondary tumors.

A "cell proliferative disorder" is any cellular disorder in which the cells proliferate more rapidly than normal tissue growth. Thus a "proliferating cell" is a cell that is proliferating more rapidly than normal cells. A proliferative disorder can include but is not limited to neoplasms.

A "neoplasm" refers to an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Unless stated otherwise, a "neoplasm" as used herein refers to all types of neoplasms. A tumor is the neoplastic growth of the disease cancer. As used herein, a neoplasm, also referred to as a "tumor", encompasses hematopoietic neoplasms as well as solid neoplasms. Other neoplasm-based disorders include, but are not limited to pancreatic cancers, neurofibromatosis, melanoma, breast cancers, head and neck cancers (e.g., brain cancers such as glioblastoma multiforme), gastrointestinal cancers and the like. A cancer generally refers to any neoplastic disorder, including such cellular disorders as, for example, pancreatic cancer, brain cancer, glioblastoma multiforme (GBM), renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer and gastrointestinal or stomach cancer.

A "subject" generally refers to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to similar or identical terms found in the incorporated references and terms expressly defined in this disclosure, the term definitions provided in this disclosure will control in all respects.

Pancreatic adenocarcinoma is one of the most common types of cancer today and has a dismal 5-year survival rate of <5%. The most common first-line agent used to treat pancreatic cancer is gemcitabine, a toxic chemotherapy that non-specifically targets rapidly dividing cells. The first-line chemotherapy has a response rate of <20%. Currently, there are no FDA approved drugs that have been developed to inhibit pancreatic cancer progression and metastasis.

Id-1 is a helix-loop-helix protein that acts as an inhibitor of basic helix-loop-helix transcription factors that control development and carcinogenesis. Id-1 has been shown to play a key role in cancer progression and development of metastasis across multiple cancers including pancreatic cancer. In a recent mRNA analysis of Id genes (Id1-4) across 36 cancer types, high (more than 10-fold) Id-1 expression was observed in many aggressive cancers including liver, glioma, breast, and pancreatic cancers. Targeting Id-1 expression also re-sensitizes multiple aggressive cancers to first-line agents. Id-1 is not expressed in differentiated/non-tumor tissue, but is highly expressed in metastatic tumor cells. Hence, reducing Id-1 provides a strong rationale for selecting Id-1 as a potential therapeutic target for treatment of aggressive pancreatic cancer. It has been found that a non-toxic plant-based compound, cannabidiol (CBD), targets cancer progression and metastasis by down-regulating Id-1 expression (preliminary data) and this activity leads to increase survival. CBD targets Id-1 gene expression at the promoter level, and that when Id-1 was expressed ectopically (not under the influence of the endogenous promoter) CBD no longer inhibited Id-1 gene expression, invasion and metastasis. This demonstrates that CBD targeting of Id-1 expression is important for the inhibition of the aggressive cancer cells. Because of this specificity, lead compounds could be screened and identified which have greater affinity for downregulating Id-1 expression and further which exhibited efficacy at inhibiting the advanced stages of metastatic progression.

The disclosure provides for resorcinol-based compounds, which in comparison to CBD, demonstrated significantly improved activity and pharmacokinetic properties for treating cancer (e.g., pancreatic cancer). The resorcinol-based compounds of the disclosure, like Compound-5B, demonstrated significant activity at targeting Id-1 expression and pancreatic cancer aggressiveness in culture. For example, in a subcutaneous xenograft model of human pancreatic cancer, Compound-5B was found to be as efficacious as gemcitabine, with a significantly improved toxicity profile.

Metastasis is the final and often fatal step in the progression of aggressive cancers. Currently available therapeutic strategies at this stage of cancer progression are often non-specific, have only marginal efficacy and are highly toxic. This is in part due to the lack of knowledge about the molecular mechanisms regulating the development of aggressive cancers. Therapeutic approaches targeting only specific mechanisms involved in the development of aggressive cancers are in urgent need. The expectation would be that this strategy would reduce unwanted toxicities associated with the therapy itself. Based on past studies and the important role Id-1 plays in controlling metastatic progression, it is expected that the resorcinol-based compounds to be more efficacious than other therapies (e.g., gemcitabine) for treating cancer metastasis.

Many current drugs targeting aggressive cancers are non-specific cytotoxics (e.g., gemcitabine) and few have been developed to specifically target invasion and metastasis. The resorcinol-based compounds of the disclosure down-regulate Id-1 expression to specifically target invasion and metastasis. Since Id-1 is not expressed in differentiated/non-tumor tissue, but is expressed in infiltrating and aggressive tumor cells, this approach significantly reduces the potential for off-target effects. The resorcinol-based compounds of the disclosure can be used to treat cancers, like pancreatic cancer, which currently lack effective therapies. Although, the resorcinol-based are expected to specifically target cell invasiveness and metastatic progression by downregulating Id-1 expression; the resorcinol-based compounds of the disclosure could also serve as excellent candidates to reduce cell proliferation. In comparison to CBD, the resorcinol-based compounds of the disclosure are more potent at targeting Id-1 and pancreatic cancer aggressiveness in culture and in vivo.

The resorcinol-based compounds disclosed herein were shown to inhibit Id-1 expression and tumor progression in a mouse model of breast cancer. In particular, the Compound-5B compound was found to be particularly effective in downregulating Id-1 expression and corresponding cell invasiveness and metastatic progression by breast cancer cells.

Compositions comprising the resorcinol-based compounds disclosed herein were found to modulate Id-1 expression in tested cancer cell lines. Moreover, as Id-1 expression was found to be up-regulated during the progression of many types of solid tumors, compositions comprising the resorcinol-based compounds disclosed herein can provide a generalized therapeutic strategy for the treatment of various aggressive cancers. Accordingly, provided herein are methods for modulating the activity of a metastatic cell by regulating the activity of a target Id polypeptide by using a resorcinol-based compound disclosed herein. For the purposes of this disclosure, "downregulating the activity of a target Id" can include: (1) mechanisms for modulating endogenous nucleic acid sequences which encode a target Id protein so that Id polypeptide levels are decreased in a cell; (2) introducing exogenous nucleic acid sequences that inhibit Id mRNA and/or protein expression in a cell; and (3) increasing the turnover rate of endogenous Id polypeptides such that Id polypeptide levels are decreased in a cell.

In a particular embodiment, the disclosure provides methods that can be used to identify substances that modulate the biological activity of an Id polypeptide, such as by modulating the expression of an Id nucleic acid sequence which encodes an Id polypeptide. In another embodiment, a method disclosed herein can be used to identify one or more resorcinol-based compounds that bind to Id regulatory sequences. In yet another embodiment, a method disclosed herein can be used to identify one or more substances which modulate the biological activity of an Id polypeptide by affecting the half-life of an Id polypeptide.

In a particular embodiment, the disclosure provides methods for treating cell proliferation disorders by administering one or more resorcinol-based compounds disclosed herein. In general, these methods can be used to treat disorders related to neoplastic cells and the metastasis thereof. In a certain embodiment, the disclosure provides methods for treating cell proliferative disorders by administering one or more resorcinol-based compounds disclosed herein which regulate the expression and/or activity of endogenous Id polypeptides and/or the half-life of endogenous Id polypeptides. In a further embodiment, the disclosure provides methods for treating disorders that can be ameliorated by modulating Id expression.

The disclosure also pertains to the field of predictive medicine in which diagnostic assays, prognostic assays, pharmacogenomics, and monitoring clinical trials are used for prognostic (predictive) purposes to thereby treat an individual prophylactically. As such, the disclosure contemplates use of methods provided herein to screen, diagnose, stage, prevent and/or treat disorders characterized by expression or over-expression of an Id helix-loop-helix polypeptide, such as Id-1. Accordingly, a subject can be screened to determine the level of a particular Id's expression or activity. A subject with a cell proliferative disorder can also be screened to determine whether abnormally proliferating cells would be susceptible to techniques disclosed herein, including inhibiting the expression or over expression of a target Id, e.g. Id-1.

The disclosure also provides for prognostic (or predictive) assays for determining whether an individual is at risk of developing a disorder associated with elevated/reduced expression of a target Id polypeptide. Such assays can be used for prognostic or predictive purpose to thereby prophylactically treat an individual prior to the onset of a disorder characterized by or associated with over expression or activity of a target Id polypeptide, such as Id-1.

As described herein the resorcinol-based compounds disclosed herein are significantly more effective than CBD and other compounds at inhibiting the expression of genes and proteins that modulate cancer aggressiveness (e.g. Id-1). The data also indicate that Id-1 is a key factor for breast cancer cell aggressiveness. The down-regulation of gene expression of Id-1 resulted from inhibiting the endogenous Id-1 promoter. As shown in the Figures presented herein, the resorcinol-based compound Compound-5B effectively inhibited the expression of Id-1 in metastatic breast cancer cells.

In a mouse model of metastasis, a detailed pharmacological assessment of the resorcinol-based compound, Compound-5B, revealed the drug's ability to significantly decrease tumor volume. This effect was found to be directly related to down-regulation of Id-1 expression in vivo. In hopes of generating more potent and efficacious therapeutic compounds for treating cell proliferative disorders, analogs based on the structure of resorcinol structure were screened for inhibiting breast cell viability/proliferation, and invasion and Id-1 expression.

Based upon initial screening assays, resorcinol-based compounds were identified that exhibit a significant effect in inhibiting Id-1 expression, inhibiting cell proliferation, inhibiting metastasis, and inhibiting invasion by various breast cancer cell lines (e.g., see FIGS. 5 and 6).

In a particular embodiment, the disclosure provides for a resorcinol-based compound having the structure of Formula I:

(I)

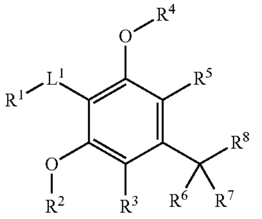

or a pharmaceutically acceptable salt, or prodrug thereof, wherein:

$L^1$ is selected from,

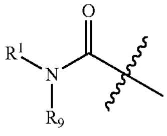,
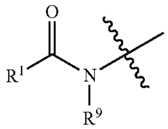,
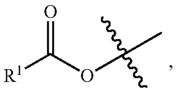, and

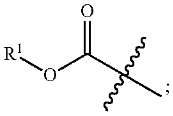;

$R^1$ is selected from H, —OH, an optionally substituted $(C_5-C_{12})$cycloalkyl, an optionally substituted $(C_5-C_{12})$ cycloalkenyl, an optionally substituted $(C_5-C_{12})$cycloalkynyl, an optionally substituted aryl, an optionally substituted heterocycle, and an optionally substituted extended mixed ring system;

$R^2$, $R^4$, $R^6$, and $R^7$ are each independently selected from H or a $(C_1-C_3)$ alkyl;

$R^3$ and $R^5$ are each independently selected from H, hydroxyl, a $(C_1-C_3)$alkyl, and a halo;

$R^8$ is selected from an optionally substituted $(C_1-C_{12})$ alkyl, an optionally substituted $(C_1-C_{11})$ hetero-alkyl, an optionally substituted $(C_1-C_{12})$ alkenyl, an optionally substituted $(C_1-C_{11})$ hetero-alkenyl, an optionally substituted $(C_1-C_{12})$alkynyl, an optionally substituted $(C_1-C_{11})$ hetero-alkynyl, an optionally substituted aryl, an optionally substituted $(C_3-C_{12})$cycloalkyl, an optionally substituted $(C_3-C_{12})$cycloalkenyl, and an optionally substituted heterocycle; and $R^9$ is selected from H, and a $(C_1-C_3)$alkyl.

In another embodiment, the disclosure provides for a resorcinol-based compound having the structure of Formula I(a):

I(a)

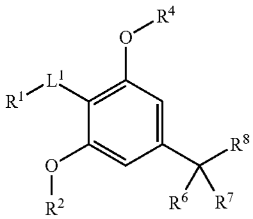

or a pharmaceutically acceptable salt, or prodrug thereof, wherein:

$L^1$ is selected from,

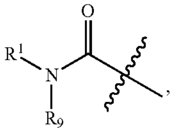, and
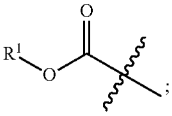;

$R^1$ is selected from H,

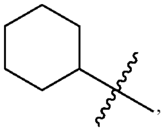,
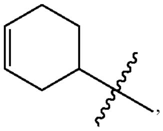,
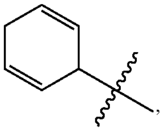,
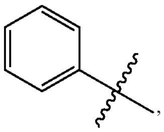,
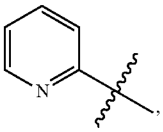,
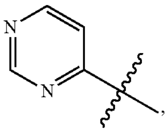,
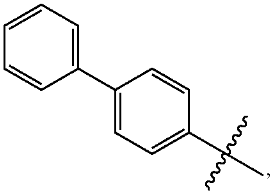,
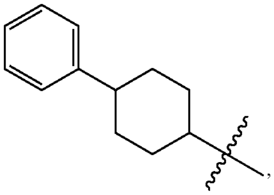,
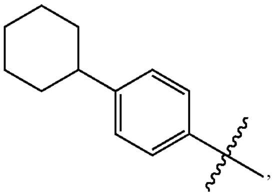,
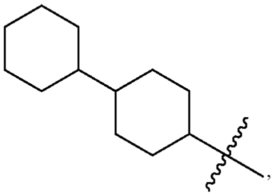,
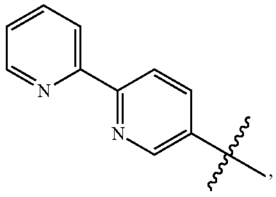, -continued

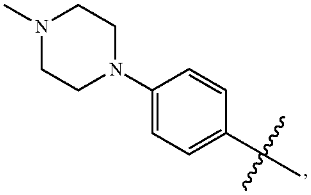,

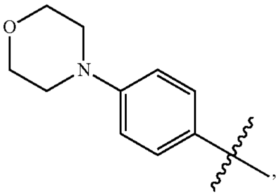, 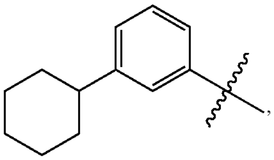,

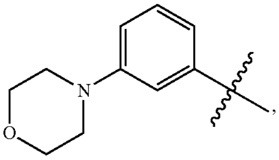,

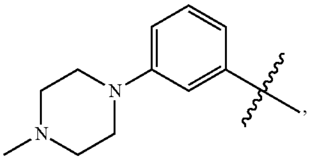, 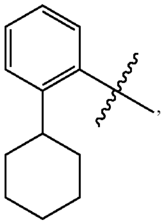,

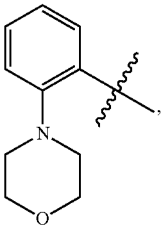, and 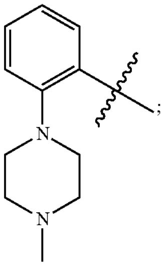;

$R^2$, $R^4$, $R^6$, and $R^7$ are each independently selected from H or a methyl group;

$R^8$ is selected from an optionally substituted ($C_1$-$C_{12}$) alkyl, an optionally substituted ($C_1$-$C_{11}$) hetero-alkyl, an optionally substituted ($C_1$-$C_{12}$) alkenyl, an optionally substituted ($C_1$-$C_{11}$) hetero-alkenyl, an optionally substituted ($C_1$-$C_{12}$)alkynyl, an optionally substituted ($C_1$-$C_{11}$) hetero-alkynyl, an optionally substituted aryl, an optionally substituted ($C_3$-$C_{12}$)cycloalkyl, an optionally substituted ($C_3$-$C_{12}$)cycloalkenyl, and an optionally substituted heterocycle; and $R^9$ is selected from H, and a ($C_1$-$C_3$)alkyl.

In another embodiment, the disclosure provides for a resorcinol-based compound having the structure of Formula I(b):

I(b)

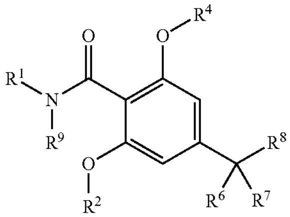

or a pharmaceutically acceptable salt, or prodrug thereof, wherein:

$R^1$ is selected from H,

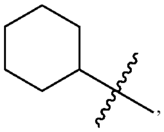, 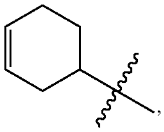, 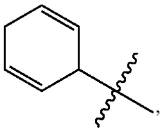,

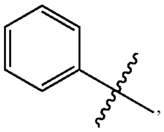, 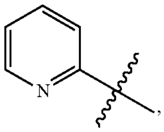, 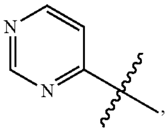,

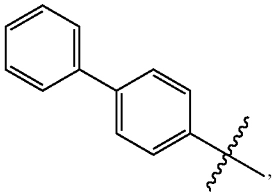, 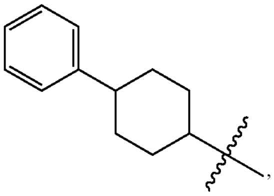,

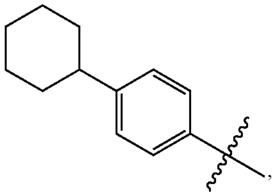, 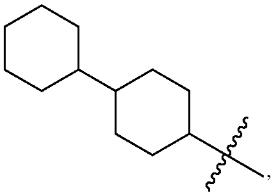,

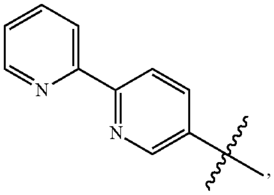,

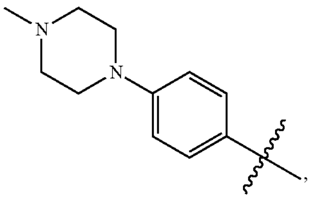,

-continued

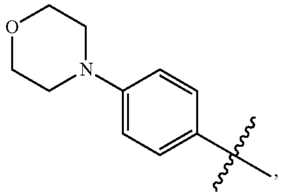,
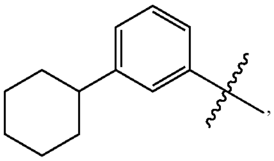,

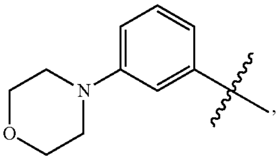,

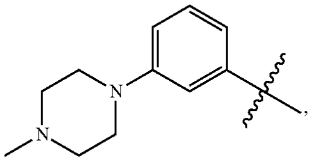,
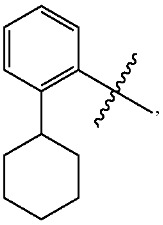,

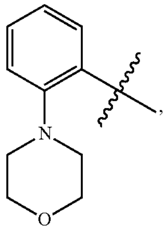, and
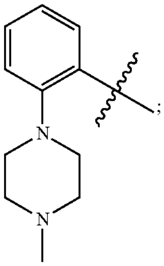;

$R^2$, $R^4$, $R^6$, and $R^7$ are each independently selected from H or a methyl group;

$R^8$ is selected from a $(C_1\text{-}C_{12})$ alkyl, a $(C_2\text{-}C_{12})$ alkenyl, a $(C_2\text{-}C_{12})$alkynyl, a $(C_3\text{-}C_8)$cycloalkyl, an aryl, a heterocycle, a $-(CH_2)_x$-aryl, a $-(CH_2)_x$-cycloalkyl, and a $-(CH_2)_x$-heterocycle, wherein X is an integer selected from 1, 2, 3, 4, 5, 6, 7, 8, 9, and 10.

$R^9$ is selected from H, and a $(C_1\text{-}C_3)$alkyl.

In a further embodiment, the disclosure provides for a resorcinol-based compound having the structure of:

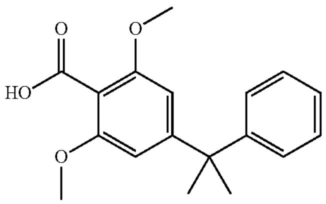,

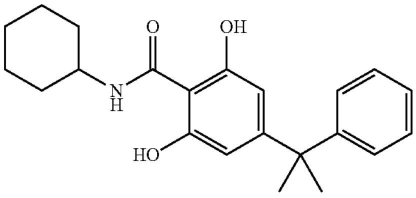,

-continued

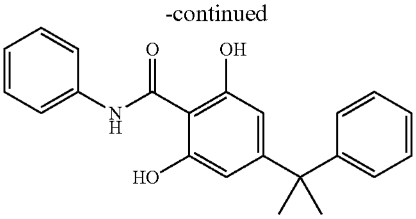,

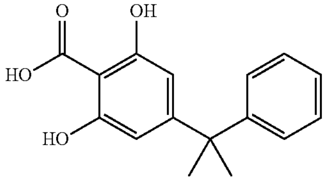,

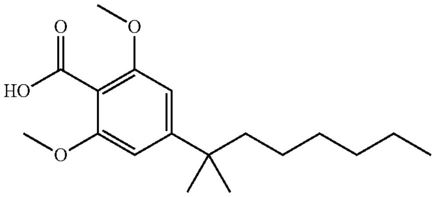,

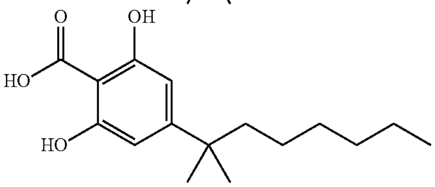,

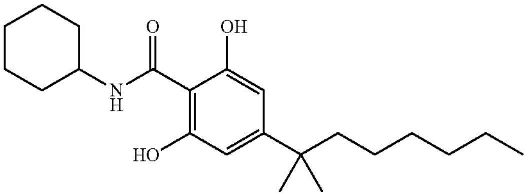,

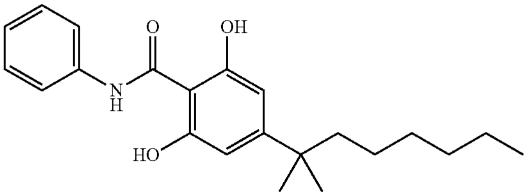,

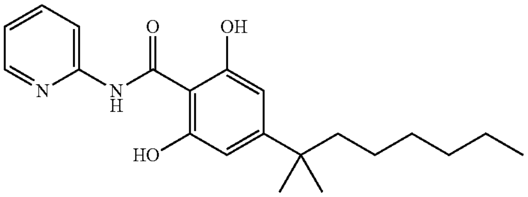,

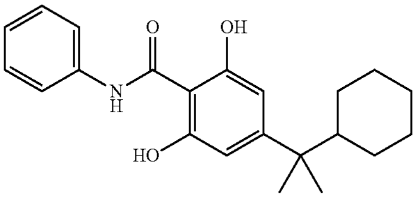,

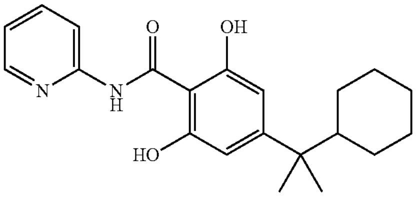,

-continued

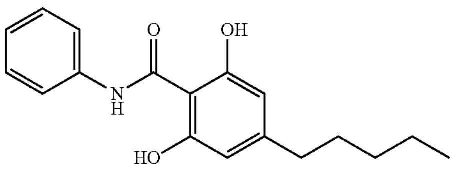

,

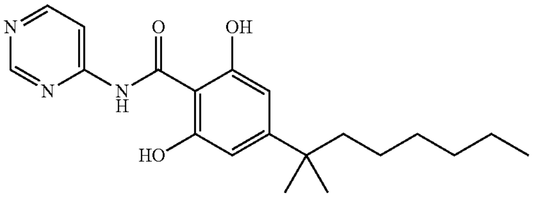

,

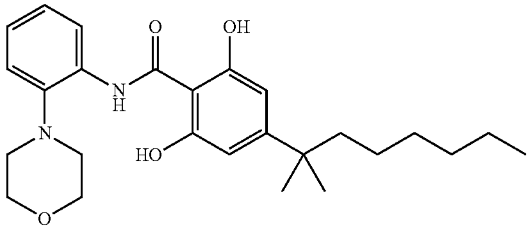

,

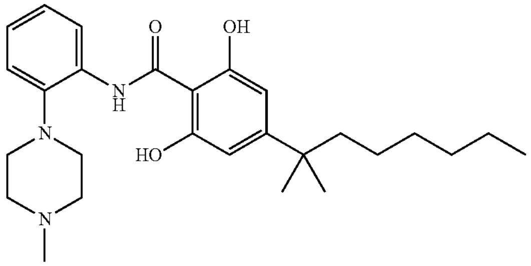

,

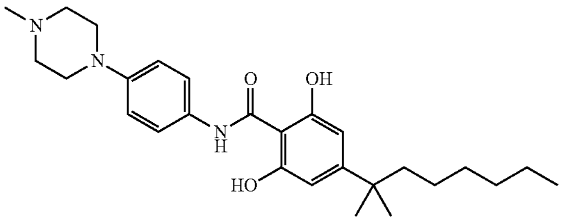

,

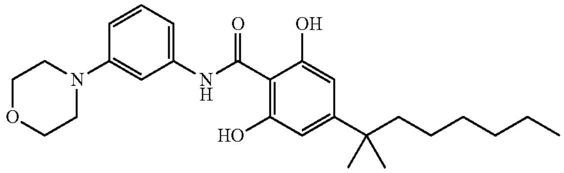

,

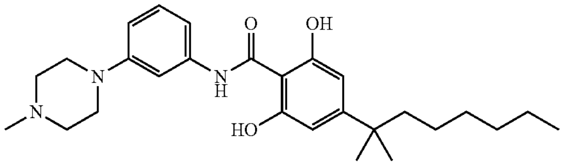

,

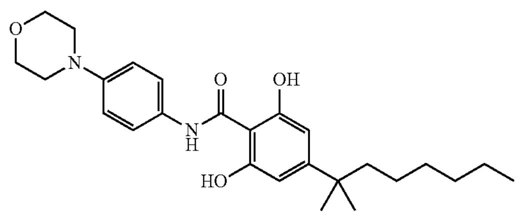

, or

-continued

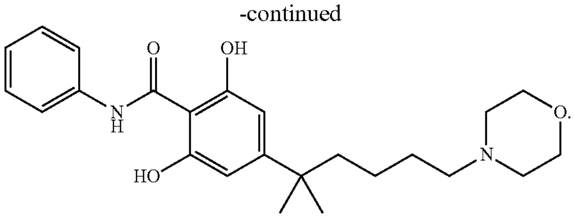

The compounds disclosed herein can be prepared by methods known to one of skill in the art and routine modifications thereof, and/or following procedures and schemes presented herein, and routine modifications thereof, and/or procedures found in international application PCT/US2002/19569, Mahadevan et al., *J. Med. Chem.* 2000, 43(2):3778-86; Ben-Shabat et al., *J. Med. Chem.* 2006, 49(3):1113-117; Wiley et al., JPET 2002, 30/(2):679-689; Thompson et al., *Synthesis* 2005 4:547-550; Razdan, Rajik, *The total synthesis of natural products* 4, 1981:186-262, and references cited therein and routine modifications thereof.

It should be understood many of the reagents and starting materials used in the Schemes presented herein are readily available from various commercial suppliers, such as Sigma-Aldrich, Alfa Aesar, Tokyo Chemical Industry Co., LTD, etc. Moreover, many of these same reagents and starting materials can be modified to incorporate additional functional groups by using standard organic synthesis reactions.

When a compound disclosed herein contains an acidic or basic moiety, it may also disclosed as a pharmaceutically acceptable salt (See, Berge et al., J. Pharm. Sci. 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (+/−)-DL-lactic acid, lactobionic acid, lauric acid, maleic acid, (−)-L-malic acid, malonic acid, (+/−)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The disclosure provides that compounds disclosed herein can have prodrug forms. Prodrugs of the compounds are useful in the methods of this disclosure. Any compound that will be converted in vivo to provide a biologically, pharmaceutically or therapeutically active form of a compound of the disclosure is a prodrug. Various examples and forms of prodrugs are well known in the art. Examples of prodrugs are found, inter alia, in *Design of Prodrugs*, edited by H. Bundgaard, (Elsevier, 1985), Methods in Enzymology, Vol. 42, at pp. 309-396, edited by K. Widder, et al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p.1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Prodrugs of compounds disclosed herein can be prepared by methods known to one of skill in the art and routine modifications thereof, and/or procedures found in U.S. Pat. No. 8,293,786, and references cited therein and routine modifications made thereof.

In a certain embodiment, a resorcinol-based compound disclosed herein can be administered directly or as a part of a composition. In other embodiments, the composition could be formulated as a pharmaceutical composition for administration to a subject. In another embodiment, a resorcinol-based compound disclosed herein can be a part of a pharmaceutical composition which includes one or more pharmaceutically acceptable carriers. Pharmaceutically acceptable carriers include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy to administer by a syringe. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, e.g. a compound disclosed herein, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, one or more compounds of the disclosure are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (e.g., the concentration of the test compound which achieves a half-maximal inhibition of symptoms) as determined in cell culture. Such information can be used to more accurately determine useful doses in humans. Levels in plasma can be measured, for example, by high performance liquid chromatography.

Compositions and formulations of one or more resorcinol-based compounds disclosed herein can be used to treat a cancer in a subject need thereof. Examples of cancers that can be treated with a resorcinol-based compound of the disclosure include, but are not limited to, pancreatic cancer, breast cancer, prostate cancer, non-small cell lung cancer, gastric cancer, melanoma, glioblastoma, hepatocarcinoma, and anaplastic thyroid tumor.

In another embodiment, a method of treating cancer in a subject comprises administering to a subject in need of such treatment a therapeutically effective amount of a pharmaceutical composition comprising one or more resorcinol-based compounds disclosed herein and a pharmaceutically acceptable carrier.

In a further embodiment, resorcinol-based compounds of the disclosure can be combined with one or more cancer therapeutics for the treatment of a cancer in a subject. Examples of cancer therapeutic agents, include, but not limited to, alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, and chemotherapeutic agents. In yet a further embodiment, resorcinol-based compounds of the disclosure can be combined with one or more anti-cancer agents. Examples of anti-cancer agents include, but are not limited to, methotrexate, fluorouracil, hydroxyurea, mercaptopurine, cisplatin, daunorubicin, doxorubicin, etoposide, vinblastine, vincristine, temozolomide, and paclitaxel.

In a particular embodiment, a pharmaceutical composition for treating a cell proliferative disorder includes a resorcinol-based compound disclosed herein and one or more cancer therapeutic agents selected from the group comprising: paclitaxel, temozolomide, methotrexate, fluorouracil, hydroxyurea, mercaptopurine, cisplatin, daunorubicin, doxorubicin, etoposide, vinblastine, vincristine and paclitaxel.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more resorcinol-based compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

EXAMPLES

Cell culture and treatment of pancreatic cancer cell lines: Pancreatic cancer cells lines BxPC-3, SW1990, and PANC-1 used in the experiments presented herein can be obtained from ATCC. The cells can be cultured and passaged in complete growth medium (RPMI-1640, Dulbecco's Modified Eagle Medium, or Leibovitz's L-15 medium) that has been supplemented with fetal bovine serum to a final concentration of 10%.

Quantitative Western analysis: Cells are cultured and treated in 6-well dishes. After the cells are washed twice with cold PBS, lysis buffer is added. The cells are then lysed by freezing for 10 min at −70° C. and then thawing at ambient temperature. The cell lysate is collected and the protein content is determined by using Bradford reagent. Equal amounts of protein are heated at 90° C. in Laemmli sample buffer which also included β-mercaptoethanol. The samples are then loaded onto a precast SDS-PAGE gel (Bio-Rad Laboratories, Hercules, CA). After which, proteins are then electroblotted onto an Immobilon membrane (Millipore, Billerica, MA) overnight at 2-4° C. The membrane is then blocked for 1 hour with 5% nonfat dry milk which included TBS+Tween. The membranes are then incubated with an anti-Id-1 primary antibody, and then an appropriate secondary antibody was used. Blots are incubated for 45 min and then washed 4 times with TBS+Tween for 15 min each. The blots are developed with SuperSignal Femto (Pierce, Rockford, IL), and imaged on either a Fluorchem 8900 (Alpha Innotech, San Leandro, CA) or ECL Hyperfilm (Amersham-Pharmacia, Piscataway, NJ). Band intensity values are obtained (after background subtraction) directly from the Fluorchem 800 using AlphaeaseFC software (San Leandro, CA) or from film using Image-J (NIH, MD). As a normalization control for loading, blots are stripped and re-probed with mouse alpha-tubulin (Abcam, Cambridge, MA) and goat anti-mouse IgG (Jackson Immunoresearch) for the primary and secondary antibodies, respectively.

General Scheme to Synthesize Resorcinol-Based Compounds

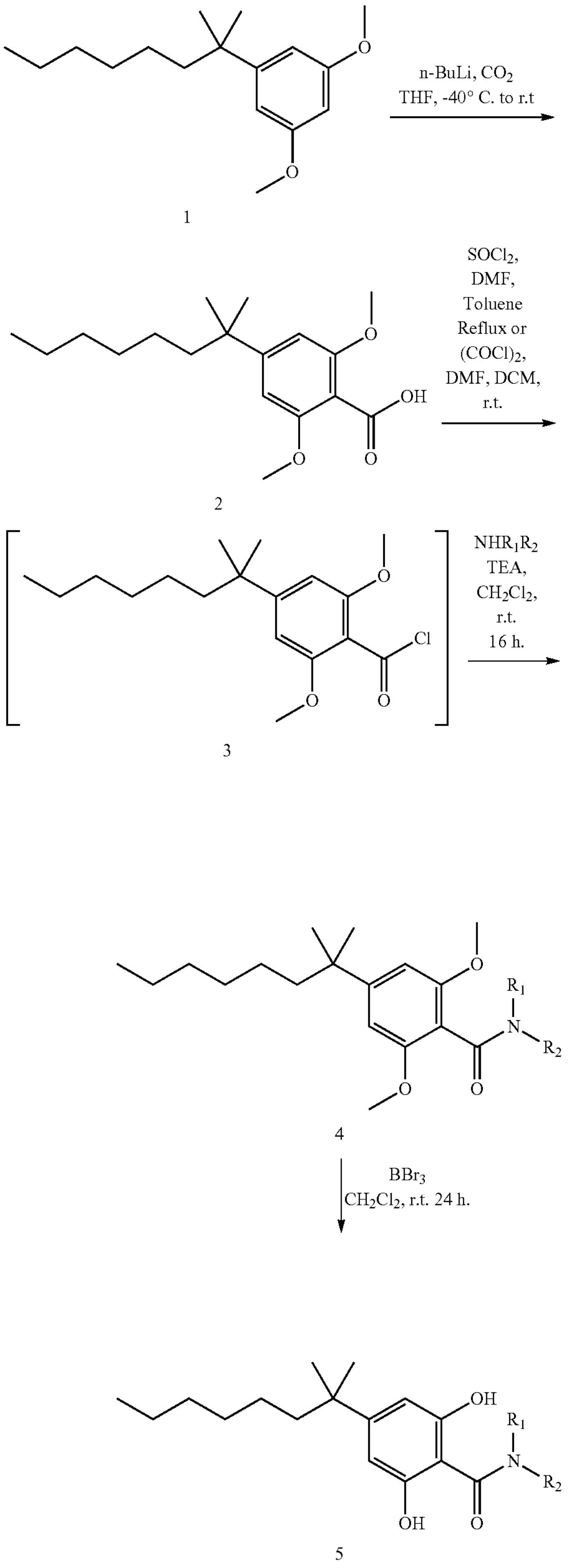

-continued $R_1$ = H, $CH_3$ $R_2$ =

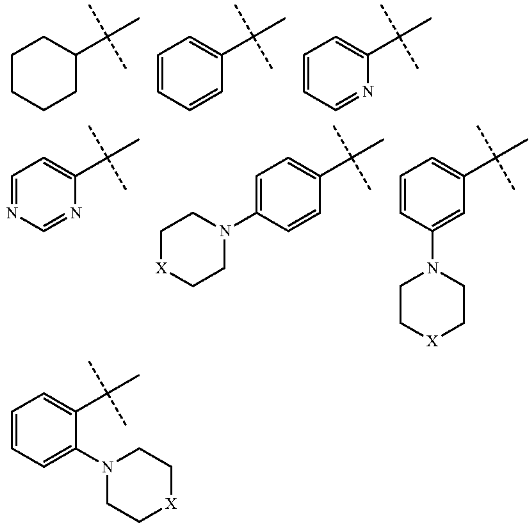

X = O, N—$CH_3$

General Procedure A—Acid Formation 2,6-dimethoxy-4-(2-methyloctan-2-yl)benzoic acid (2)

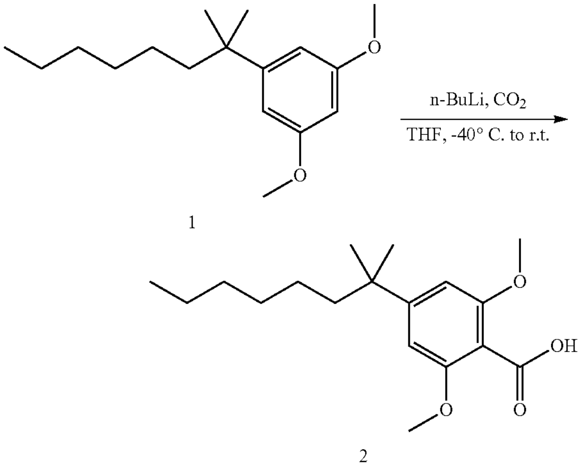

Under a nitrogen atmosphere and at −40° C., n-butyl lithium (15.1 mL, 2.5 M in hexane, 37.82 mmol) was added dropwise to a solution of 1,3-dimethoxy-5-(1,1-dimethyl-heptyl)benzene (5.00 g, 18.91 mmol) in dry THF (150 mL). The solution was slowly warmed to ambient temperature and stirred for 5.5 hours. The reaction mixture was then poured over excess dry ice that had been washed with $Et_2O$ in a 500 mL Erlenmeyer flask. The flask was loosely covered with Parafilm, and the mixture was slowly warmed to ambient temperature and stirred overnight. The reaction mixture was then quenched with methanol (50 mL), transferred to a round bottom flask, and concentrated in vacuo to afford an off-white powder. The solid was then suspended in 1 M HCl (50 mL) and extracted into ethyl acetate (150 mL). The organic phase was then washed with 3×50 mL water and 50 mL brine, dried over $MgSO_4$, and concentrated in vacuo to produce an off-white powder. Trituration of the solid with hexanes (100 mL) yielded the title product as a white solid (4.38 g, 75% yield). $^1$H NMR (300 MHz, $CDCl_3$) δ0.85 (3H, t, J=6.7 Hz), 1.05 (2H, m), 1.25 (12H, m) 1.55 (2H, m), 3.91 (6H, s), 6.56 (2H, s). MS ($M+H^+$) m/z: 309.2 (100%).

General Procedure B—Amide Bond Formation

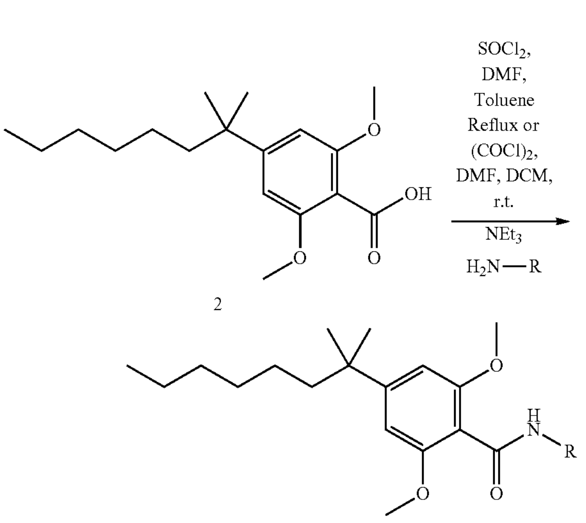

2

4

Oxalyl chloride (0.15 mL, 1.70 mmol) or thionyl chloride (1.7 mmol) and N,N-dimethylformamide (0.02 mL, 0.162 mmol) were added to a solution of 2,6-dimethoxy-4-(2-methyloctan-2-yl)benzoic acid (500 mg, 1.62 mmol) in dichloromethane (8 mL). The reaction was stirred for three hours at ambient temperature. Upon complete formation of the acid chloride, as confirmed through mass spectral analysis of an aliquot of the reaction quenched with methanol, the respective amine (1.95 mmol) and triethylamine (0.18 mL, 1.25 mmol,) were added portion-wise to the reaction mixture, and the reaction mixture was stirred at ambient temperature overnight. Upon reaction completion, as observed through mass spectral analysis, the reaction was quenched with 6 mL saturated sodium bicarbonate. The organic phase was washed with 6 mL each of saturated sodium bicarbonate, water, and brine. The organic phase was then dried over $MgSO_4$, and concentrated in vacuo. After which, the crude product was purified using automated flash chromatography using a 40 g column and gradient dichloromethane-methanol solvent system.

N-Cyclohexyl-2,6-dimethoxy-4-(2-methyloctan-2-yl)benzamide (4A)

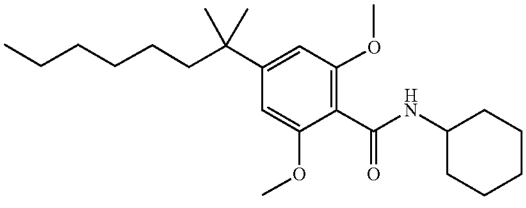 [SMILES: CCCCCCC(C)(C)c1cc(OC)c(C(=O)NC2CCCCC2)c(OC)c1]

The title product was synthesized via general procedure B using an intermediate acid chloride (450 mg, 1.3 mmol), and cyclohexylamine (0.520 g, 5.2 mmol). After completion of reaction, the solvent was removed under vacuum and the resulting residue was dissolved in ethyl acetate and washed with dilute HCl (5%) and water. The ethyl acetate layer was dried over sodium sulfate. The ethyl acetate was removed under vacuum and the resulting residue was purified using column chromatography with a gradient of ethyl acetate in hexanes. The title product was isolated as a white solid. 340 mg (57% yield). $^1$H NMR (300 MHz, $CDCl_3$) δ0.82-0.86 (t, 3H), 1.19-1.25 m, 18H), 1.53-1.58 (m, 4H), 2.07-1.72 (m, 4H), 3.8 (s, 6H), 4.05 (s, 1H), 5.58 (d, 1H), 6.48 (s, 2H). MS ($M+H^+$) m/z: 390.2 (100%).

2,6-dimethoxy-4-(2-methyloctan-2-yl)-N-phenylbenzamide (4B)

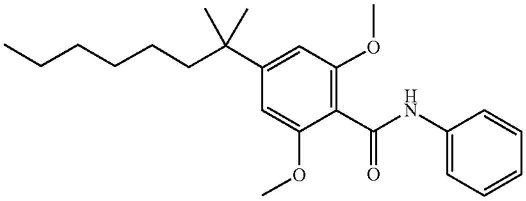 [SMILES: CCCCCCC(C)(C)c1cc(OC)c(C(=O)Nc2ccccc2)c(OC)c1]

The title product was synthesized via general procedure B using an intermediate acid chloride (450 mg, 1.3 mmol), and aniline (0.7 g, 7.5 mmol). After the completion of reaction, the solvent was removed under vacuum and the resulting residue was dissolved in ethyl acetate and washed with dilute HCl (5%) and water. The ethyl acetate layer was dried over sodium sulfate and the ethyl acetate was removed under vacuum. The resulting residue was purified using column chromatography with a gradient of ethyl acetate in hexanes. The title product was isolated as a white solid. 390 mg (78% yield). $^1$H NMR (300 MHz, $CDCl_3$) δ0.82-0.85 (m, 3H), 1.15-1.19 (m, 12H), 1.45-1.54 (m, 4H), 3.6 (s, 6H), 6.48 (s, 2H), 7.10 (t, 1H), 7.33 (t, 2H), 7.5 (s, 1H), 7.65 (d, 2H). MS ($M+H^+$) m/z: 384.2 (100%).

2,6-dimethoxy-4-(2-methyloctan-2-yl)-N-(pyridin-2-yl)benzamide (4C)

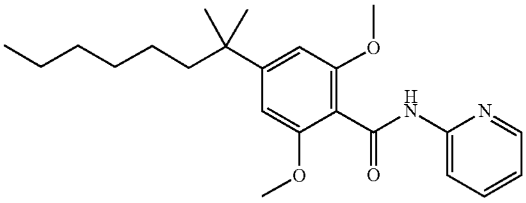 [SMILES: CCCCCCC(C)(C)c1cc(OC)c(C(=O)Nc2ccccn2)c(OC)c1]

The title product was synthesized via general procedure B using an acid chloride intermediate (900 mg, 2.91 mmol) and 2-aminopyridine (750 mg, 7.96 mmol). After completion of reaction, the solvent was removed under vacuum and the resulting residue was dissolved in ethyl acetate and washed with dilute HCl (5%) and water. The ethyl acetate layer was dried over sodium sulfate and removed under vacuum. The resulting residue was purified using column chromatography with a gradient of ethyl acetate in hexanes.

The title product was isolated as a light brown solid. 428 mg (38% yield). The product was used directly in the next step without further characterization.

2,6-dimethoxy-4-(2-methyloctan-2-yl)-N-(pyrimidin-4-yl)benzamide(4D)

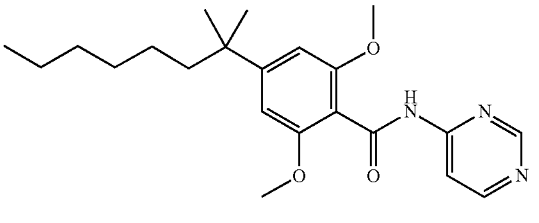 [SMILES: CCCCCCC(C)(C)c1cc(OC)c(C(=O)Nc2ccncn2)c(OC)c1]

The title product was synthesized via general procedure B using an acid chloride intermediate (500 mg, 1.53 mmol), 4-aminopyrimidine (218.8 mg, 2.3 mmol) and $NEt_3$ (0.24 mL, 1.68 mmol). The title product was isolated as an off white colored solid (460 mg, 79% yield). $^1H$ NMR (300 MHz, $CDCl_3$) δ0.82-0.85 (m, 3H), 1.15-1.19 m, 12H), 1.45-1.54 (m, 4H), 3.37 (s, 6H), 6.45 (s, 2H), 7.99 (d, J=6.2 Hz, 1H), 8.31 (d, J=6.2 Hz, 1H), 8.75 (s, 1H); MS ($M+H^+$) m/z: 386.2 (100%).

2,6-dimethoxy-N-methyl-4-(2-methyloctan-2-yl)-N-phenylbenzamide (4E)

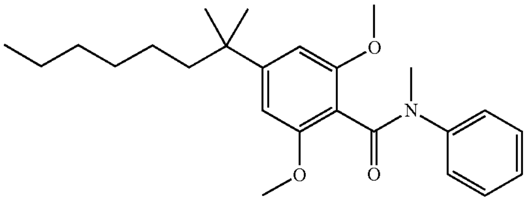 [SMILES: CCCCCCC(C)(C)c1cc(OC)c(C(=O)N(C)c2ccccc2)c(OC)c1]

The title product was synthesized via general procedure B using an acid chloride intermediate (400 mg, 1.29 mmol), N-methylaniline (0.13 mL, 1.41 mmol) and $NEt_3$ (0.23 mL, 1.41 mmol). The crude product was purified using a CombiFlash gradient of ethyl acetate in hexanes to afford the title product as a brown oil (420 mg, 80% yield). $^1H$ NMR (300 MHz, $CDCl_3$) δ0.83 (t, J=6.6 Hz, 3H), 1.08-1.19 (m, 14H), 1.21-1.25 (m, 2H), 3.28 (s, 3H), 3.64 (s, 6H), 6.29 (s, 2H), 7.29-7.12 (m, 5H); MS ($M+H^+$) m/z: 398.3 (100%).

2,6-dimethoxy-4-(2-methyloctan-2-yl)-N-(4-(4-methylpiperazin-1-yl)phenyl)benzamide (4F)

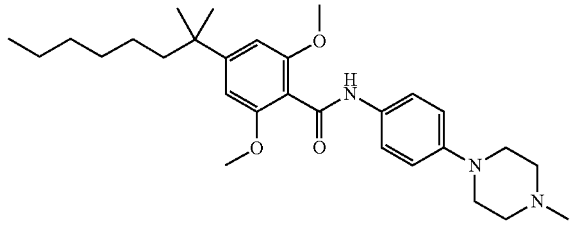 [SMILES: CCCCCCC(C)(C)c1cc(OC)c(C(=O)Nc2ccc(N3CCN(C)CC3)cc2)c(OC)c1]

The title product was synthesized via general procedure B using an acid chloride intermediate (0.745 mmol) and 4-(4-methylpiperazin-1-yl)aniline (171.2 mg, 0.894 mmol, Alfa). The title product was isolated as a sticky yellow solid (257.1 mg, 68% yield). $^1H$ NMR (300 MHz, $CDCl_3$) δ0.85 (6H, m), 1.25 (14H, m), 2.49 (3H, s), 2.80 (4H, t, J=4.7 Hz), 3.28 (4H, t, J=4.6 Hz), 3.53 (6H, s), 6.53 (2H, s), 6.91 (2H, d, J=8.8 Hz), 7.55 (2H, d, J=8.8 Hz). MS ($M+H^+$) m/z: 482.3 (100%).

2,6-dimethoxy-4-(2-methyloctan-2-yl)-N-(3-(4-methylpiperazin-1-yl)phenyl)benzamide (4G)

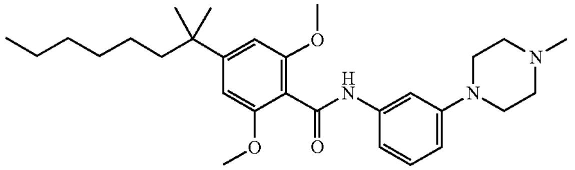 [SMILES: CCCCCCC(C)(C)c1cc(OC)c(C(=O)Nc2cccc(N3CCN(C)CC3)c2)c(OC)c1]

The title product was synthesized via general procedure B using an acid chloride intermediate and 3-(4-methylpiperazin-1-yl)aniline (260.5 mg). The title product was isolated as an off-white solid (327 mg, 60% yield). $^1H$ NMR (300 MHz, $CDCl_3$) δ0.85 (3H, t, J=6.3 Hz), 1.21 (12H, m), 1.62 (4H, m) 2.35 (3H, s) 2.57 (4H, t, J=5.2 Hz), 3.25 (4H, t, J=5.2 Hz), 3.82 (6H, s), 6.53 (2H, s), 6.65 (1H, d, J=8.2 Hz), 6.88 (1H, d, 7.8 Hz), 7.19 (1H, t, 8.2 Hz), 7.46 (1H, s), 7.56 (1H, s). MS ($M+H^+$) m/z: 482.3 (100%).

2,6-dimethoxy-4-(2-methyloctan-2-yl)-N-(3-(4-methylpiperazin-1-yl)phenyl)benzamide (4H)

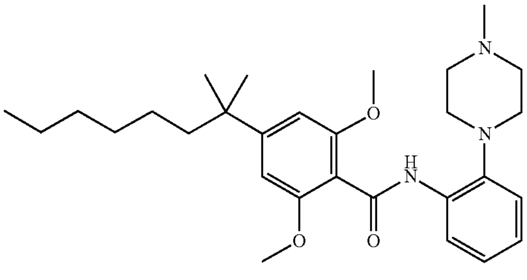 [SMILES: CCCCCCC(C)(C)c1cc(OC)c(C(=O)Nc2ccccc2N2CCN(C)CC2)c(OC)c1]

The title product was synthesized via general procedure B using an acid chloride intermediate and 2-(4-methylpiperazin-1-yl)aniline (260.5 mg). The title product was isolated as a sticky, red-orange solid (375.1 mg, 69% yield). $^1H$ NMR (300 MHz, $CDCl_3$) δ0.87 (3H, t, J=6.5 Hz), 1.11 (3H, m), 1.27 (13H, m), 1.61 (6H, s), 2.31 (3H, s) 2.51 (4H, s, br), 2.94 (4H, t, J=4.7 Hz), 3.82 (6H, s), 6.57 (2H, s) 7.06 (1H, t, J=6.57), 7.17 (1H, t, J=8.52 Hz), 8.58 (2H, m). MS ($M+H^+$) m/z: 482.3 (100%).

2,6-dimethoxy-4-(2-methyloctan-2-yl)-N-(4-morpholinophenyl)benzamide (4I)

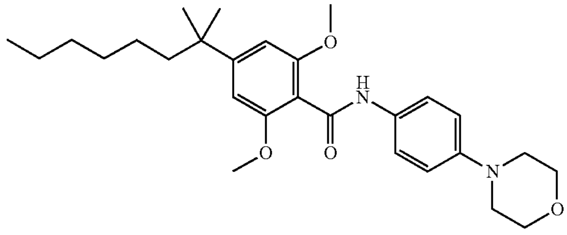 [SMILES: CCCCCCC(C)(C)c1cc(OC)c(C(=O)Nc2ccc(N3CCOCC3)cc2)c(OC)c1]

The title product was synthesized via general procedure B using an acid chloride intermediate and 4-morpholinoaniline (242.8 mg). The title product was isolated as an olive-colored foam (598 mg, 79% yield). $^1$H NMR (300 MHz, $CDCl_3$) δ0.85 (3H, t, J=6.7 Hz), 1.07 (2H, m), 1.25 (10H, m), 3.11 (4H, t, J=4.8 Hz), 3.84 (10H, m), 6.54 (2H, s), 6.89 (2H, d, J=9.0 Hz), 7.40 (1H, s), 7.56 (2H, d, J=8.8 Hz). MS (M+H$^+$) m/z: 469.3 (100%).

2,6-dimethoxy-4-(2-methyloctan-2-yl)-N-(3-morpholinophenyl)benzamide (4J)

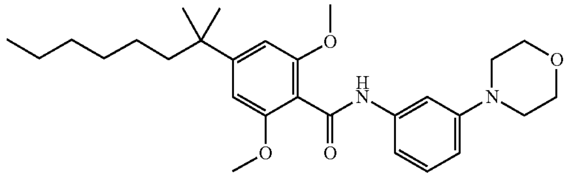 [SMILES: CCCCCCC(C)(C)c1cc(OC)c(C(=O)Nc2cccc(N3CCOCC3)c2)c(OC)c1]

The title product was synthesized via general procedure B using an acid chloride intermediate and 3-morpholinoaniline (242.8 mg). The title product was isolated as an orange-tan foam (367 mg, 48% yield). $^1$H NMR (300 MHz, $CDCl_3$) δ0.86 (3H, m), 1.09 (2H, m), 1.25 (13H, m) 1.60 (3H, m) 1.19 (4H, t, J=4.7 Hz), 3.82 (10H, m), 6.54 (2H, s) 6.65 (1H, d, J=8.3 Hz), 6.85 (1H, d J=7.6 Hz), 7.20 (1H, t, J=8.0 Hz), 7.48 (1H, s), 7.61 (1H, s). MS (M+H$^+$) m/z: 469.3 (100%).

2,6-dimethoxy-4-(2-methyloctan-2-yl)-N-(2-morpholinophenyl)benzamide (4K)

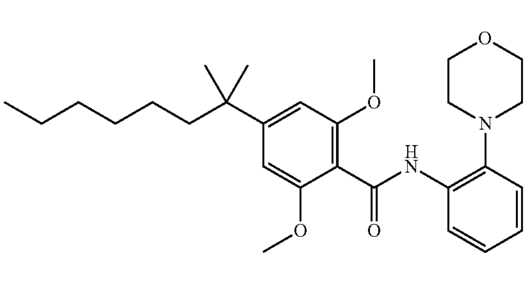 [SMILES: CCCCCCC(C)(C)c1cc(OC)c(C(=O)Nc2ccccc2N2CCOCC2)c(OC)c1]

The title product was synthesized via general procedure B using an acid chloride intermediate and 2-morpholinoaniline (346 mg). The title product was isolated as a very viscous, sticky white foam (384 mg, 51% yield). $^1$H NMR (300 MHz, $CDCl_3$) δ0.86 (3H, t, J=6.5 Hz), 1.10 (s, br, 2H), 1.27 (12H, m), 1.60 (3H, m), 2.91 (4 h, t, J=4.4 Hz), 3.79 (10H, m), 6.57 (2H, s), 7.12 (3H, m), 8.55 (1H, d, J=7.9), 8.60 (1H, s). MS (M+H$^+$) m/z: 469.3 (100%).

General Procedure C—Demethylation

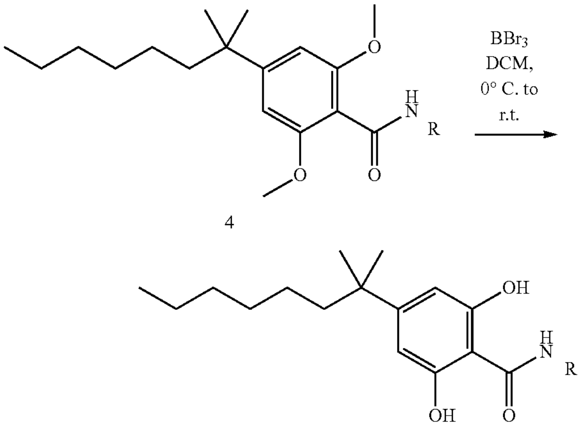

4

5

Under a nitrogen atmosphere, boron tribromide (0.445 mL, 4.69 mmol) was added to a 0° C. solution of the amide reactant (250 mg, 0.469-0.519 mmol) in anhydrous DCM (5 mL). The solution was stirred for 1 h at 0° C. and then slowly warmed to ambient temperature and stirred for an additional 23 h. Upon reaction completion, as observed through mass spectral analysis, the reaction was slowly quenched with methanol (2 mL) or ice-cold water and extracted in dichloromethane. The product was washed with water and brine. Dichloromethane was concentrated in vacuo and purified through either normal phase using gradient methanol in dichloromethane or ethyl acetate in hexanes or reverse phase flash chromatography to yield the desired product.

N-cyclohexyl-2,6-dihydroxy-4-(2-methyloctan-2-yl)benzamide (5A)

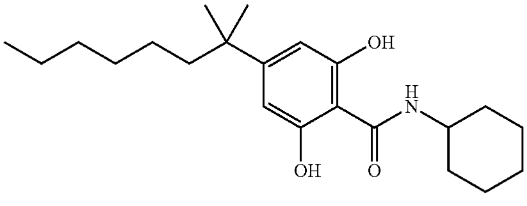 [SMILES: CCCCCCC(C)(C)c1cc(O)c(C(=O)NC2CCCCC2)c(O)c1]

The title product was synthesized via general procedure C using cyclohexyl-2,6-dimethoxy-4-(2-methyloctan-2-yl)benzamide. The crude product was purified with normal phase flash chromatography to yield the product as a cream color powder (230 mg, 89% yield). $^1$H NMR (300 MHz, $d_6$ DMSO) δ0.81 (t, 3H), 0.94-0.97 (m, 2H), 1.15 (s, 12H), 1.24-1.86 (m, 12H), 3.84 (m, 1H), 6.31 (s, 2H), 8.74 (d, J=7.1 Hz, 1H), 12.47 (s, 2H); MS (M+H$^+$) m/z: 362.2 (100%).

2,6-dihydroxy-4-(2-methyloctan-2-yl)-N-phenylbenzamide (5B)

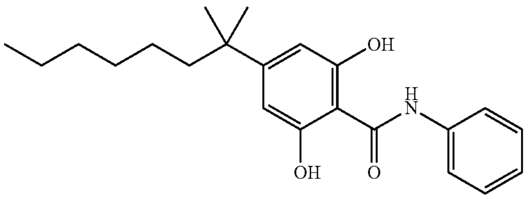 [SMILES: CCCCCCC(C)(C)c1cc(O)c(C(=O)Nc2ccccc2)c(O)c1]

The title product was synthesized via general procedure C using 2,6-dimethoxy-4-(2-methyloctan-2-yl)-N-phenylbenzamide (250 mg). The crude product was purified with normal phase flash chromatography to yield the title product as a gummy solid. (215 mg, 92% yield). $^1$H NMR (300 MHz, $d_6$ DMSO) δ0.82 (t, 3H), 0.96-1.02 (m, 2H), 1.17 (s, 12H), 1.48-1.53 (m, 2H), 6.40 (s, 2H), 7.15 (t, 1H), 7.38 (t, 2H), 7.64 (d, J=7.1 Hz, 2H), 10.71 (s, 1H), 12.28 (s, 2H); MS (M+H$^+$) m/z: 356 (100%).

2,6-dihydroxy-4-(2-methyloctan-2-yl)-N-(cyridin-2-yl) benzamide (5C)

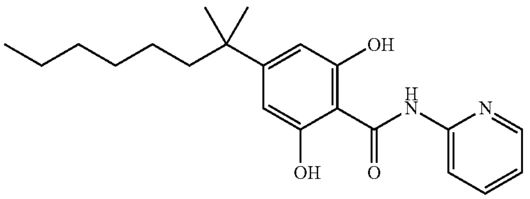 [SMILES: CCCCCCC(C)(C)c1cc(O)c(C(=O)Nc2ccccn2)c(O)c1]

The title product was synthesized via general procedure C using 2,6-dimethoxy-4-(2-methyloctan-2-yl)-N-(pyridin-2-yl)benzamide. The crude product was purified with normal phase flash chromatography to yield the title product as a white solid. (268 mg, 85% yield). $^1$H NMR (300 MHz, $d_6$ DMSO) δ0.83 (t, 3H), 0.95-1.10 (m, 2H), 1.2 (s, 12H), 1.49-1.52 (m, 2H), 6.43 (s, 2H), 7.24 (m, 1H), 7.87 (t, 1H), 8.18 (d, J=8.25 Hz, 1H), 8.37 (d, J=5.52 Hz, 1H), 11.31 (s, 1H), 12.43 (s, 2H); MS (M+H$^+$) m/z: 357 (100%).

2,6-dihydroxy-4-(2-methyloctan-2-yl)-N-(pyrimidin-4-yl)benzamide (5D)

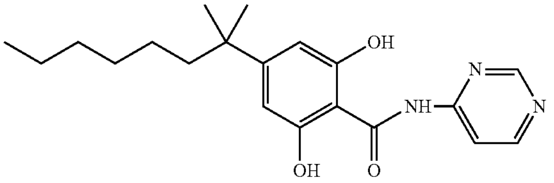 [SMILES: CCCCCCC(C)(C)c1cc(O)c(C(=O)Nc2ccncn2)c(O)c1]

The title product was synthesized via general procedure C using 2,6-dimethoxy-4-(2-methyloctan-2-yl)-N-(pyrimidin-4-yl)benzamide (460 mg, 1.19 mmol) and BBr 3 (0.6 mL, 5.95 mmol). The crude product was purified using CombiFlash normal phase chromatography to yield the title product as a white powder (163 mg, 99% purity, 59% yield). $^1$H NMR (300 MHz, $d_6$ DMSO) δ0.81 (t, J=5.9 Hz, 3H), 0.99-1.15 (m, 2H), 1.19 (s, 12H), 1.49-1.54 (m, 2H), 6.45 (s, 2H), 8.20 (d, J=6.2 Hz, 1H), 8.79 (d, J=6.0 Hz, 1H), 8.99 (s, 1H), 11.45 (s, 1H), 12.14 (br s, 2H); MS (M+H$^+$) m/z: 358 (100%).

2,6-dihydroxy-N-methyl-4-(2-methyloctan-2-yl)-N-phenylbenzamide (5E)

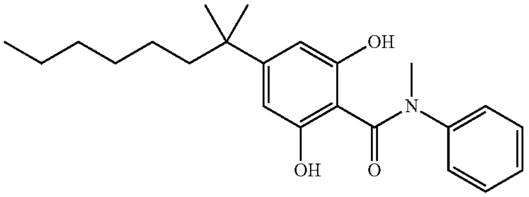 [SMILES: CCCCCCC(C)(C)c1cc(O)c(C(=O)N(C)c2ccccc2)c(O)c1]

The title product was synthesized via general procedure C using 2,6-dimethoxy-N-methyl-4-(2-methyloctan-2-yl)-N-phenylbenzamide and $BBr_3$ (0.45 mL, 5.05 mmol). The crude product was purified by CombiFlash using 0-100% Hexanes:EtOAc solvent system to afford the title product as an off white powder (210 mg, 54% yield). $^1$H NMR (300 MHz, $d_6$ DMSO) δ0.83 (t, J=6.7 Hz, 3H), 1.08-1.19 (m, 16H), 3.25 (s, 3H), 6.06 (s, 2H), 7.05-7.34 (m, 5H), 9.15 (s, 2H); MS (M+H$^+$) m/z: 370.2 (100%).

2,6-dihydroxy-4-(2-methyloctan-2-yl)-N-(4-(4-methylpiperazin-1-yl)phenyl)benzamide (5F)

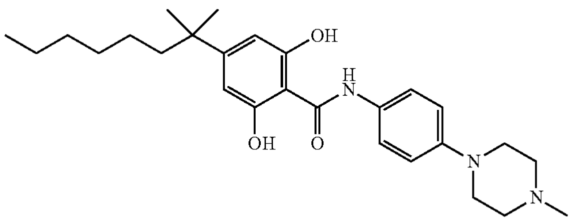 [SMILES: CCCCCCC(C)(C)c1cc(O)c(C(=O)Nc2ccc(N3CCN(C)CC3)cc2)c(O)c1]

The title product was synthesized via general procedure C using 2,6-dimethoxy-4-(2-methyloctan-2-yl)-N-(4-(4-methylpiperazin-1-yl)phenyl)benzamide and $BBr_3$. The crude product was purified with normal phase flash chromatography to yield the title product as a white powder (80 mg, 34% yield). $^1$H NMR (300 MHz, $d_6$-DMSO) δ0.81 (3H, t, J=6.0 Hz), 1.00 (2H); MS (M+H$^+$) m/z: 454.2 (100%).

2,6-dihydroxy-4-(2-methyloctan-2-yl)-N-(3-(4-methylpiperazin-1-yl)phenyl)benzamide (5G)

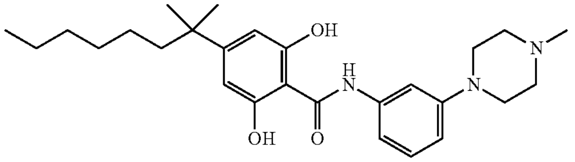 [SMILES: CCCCCCC(C)(C)c1cc(O)c(C(=O)Nc2cccc(N3CCN(C)CC3)c2)c(O)c1]

The title product was synthesized via general procedure C using 2,6-dimethoxy-4-(2-methyloctan-2-yl)-N-(3-(4-methylpiperazin-1-yl)phenyl)benzamide and $BBr_3$. The crude product was purified with normal phase flash chromatography to yield the title product as an off-white powder (145.3 mg, 62% yield). $^1H$ NMR (300 MHz, $CDCl_3$) δ0.84 (3H, t, J=6.7 Hz), 1.05 (2H, m), 1.20 (13H, m), 1.52 (2H, m), 2.52 (3H, s), 2.87 (4H, s), 3.36 (4H, s), 6.27 (2H, s), 6.53 (1H, s), 6.68 (1H, d, J=8.3 Hz), 7.22 (1H, t, J=8.3 Hz), 7.62 (1H, d, J=8.0 Hz); MS ($M+H^+$) m/z: 454.3 (100%).

2,6-dihydroxy-4-(2-methyloctan-2-yl)-N-(2-(4-methylpiperazin-1-yl)phenyl)benzamide (5H)

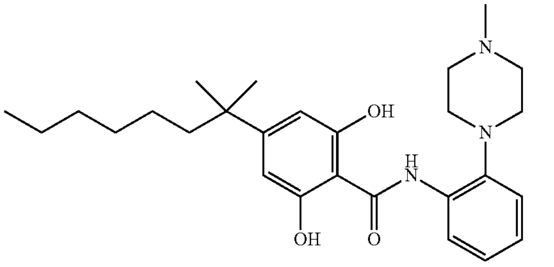 [SMILES: CCCCCCC(C)(C)c1cc(O)c(C(=O)Nc2ccccc2N2CCN(C)CC2)c(O)c1]

The title product was synthesized via general procedure C using 2,6-dimethoxy-4-(2-methyloctan-2-yl)-N-(3-(4-methylpiperazin-1-yl)phenyl)benzamide. The crude product was purified using normal phase flash chromatography to yield the title product as a tan powder (100 mg, 42% yield). $^1H$ NMR (300 MHz, $CDCl_3$) δ0.82 (3H, t, J=6.7 Hz), MS ($M+H^+$) m/z: 454.3 (100%).

2,6-dihydroxy-4-(2-methyloctan-2-yl)-N-(4-morpholinophenyl)benzamide (5I)

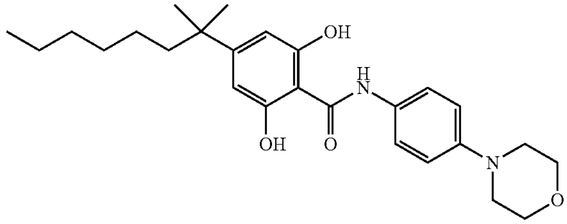 [SMILES: CCCCCCC(C)(C)c1cc(O)c(C(=O)Nc2ccc(N3CCOCC3)cc2)c(O)c1]

The title product was synthesized via general procedure C using 2,6-dimethoxy-4-(2-methyloctan-2-yl)-N-(4-morpholinophenyl)benzamide and $BBr_3$. The crude product was purified using reverse phase flash chromatography to yield the title product as a tan powder (60 mg, 25% yield). $^1H$ NMR (300 MHz, $CDCl_3$) δ0.83 (3H, t, J=6.6 Hz), 1.05 (2H, m), 1.20 (13H, m), 1.48 (2H, m), 3.11 (4H, t, J=4.8 Hz), 3.87 (4H, t, J=4.7 Hz), 6.41 (2H, s), 6.88 (2H, d, J=9.1 Hz), 7.44 (2H, d, J=8.8 Hz), 10.09 (1H, s); MS ($M+H^+$) m/z: 441.2 (100%).

2,6-dihydroxy-4-(2-methyloctan-2-yl)-N-(3-morpholinophenyl)benzamide (5J)

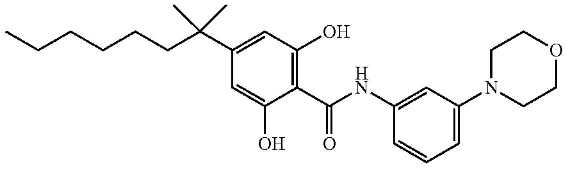 [SMILES: CCCCCCC(C)(C)c1cc(O)c(C(=O)Nc2cccc(N3CCOCC3)c2)c(O)c1]

The title product was synthesized via general procedure C using 2,6-dimethoxy-4-(2-methyloctan-2-yl)-N-(3-morpholinophenyl)benzamide and $BBr_3$. The crude product was purified using reverse phase flash chromatography to afford the title product as a tan power (60 mg, 23% yield). $^1H$ NMR (300 MHz, $CDCl_3$) δ0.83 (3H, t, J=6.7 Hz), 1.04 (2H, m), 1.20 (13H, m), 1.51 (2H, m), 3.34 (4H, t, J=4.5 Hz), 3.99 (4H, t, J=4.5 Hz), 6.42 (2H, s), 6.97 (2H, m), 7.26 (1H, t, J=9.6 Hz), 7.78 (1H, s), 10.45 (1H, s); $^{19}F$ NMR (282 MHz, $CDCl_3$) δ-75.44; MS ($M+H^+$) m/z: 441.2.

2,6-dihydroxy-4-(2-methyloctan-2-yl)-N-(2-morpholinophenyl)benzamide (5K)

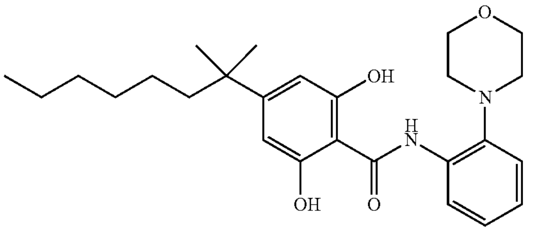 [SMILES: CCCCCCC(C)(C)c1cc(O)c(C(=O)Nc2ccccc2N2CCOCC2)c(O)c1]

The title product was synthesized via general procedure C using 2,6-dimethoxy-4-(2-methyloctan-2-yl)-N-(2-morpholinophenyl)benzamide. The crude product was purified using normal phase flash chromatography to yield the title product as an off-white powder (145.5 mg, 77% yield). $^1H$ NMR (300 MHz, $CDCl_3$) δ0.83 (3H, t, J=6.6 Hz), 1.08 (1H, m), 1.20 (12H, m), 1.53 (2H, m), 1.79 (1H, s, br.), 3.04 (4H, t, J=4.1 Hz), 4.08 (4H, t, J=4.1 Hz), 6.48 (2H, s), 7.21 (3H, m), 8.53 (1H, t, J=2.0 Hz), 11.15 (1H, s); MS ($M+H^+$) m/z: 441.2.

Scheme-2

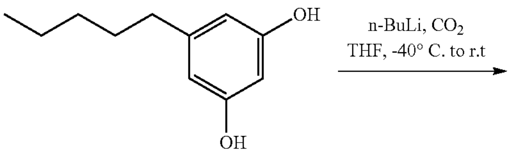

8

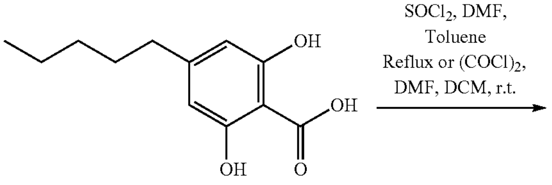

9

-continued

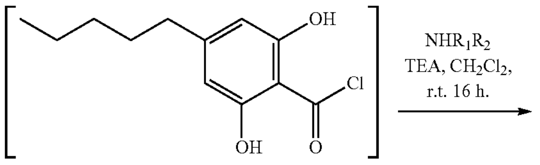

10

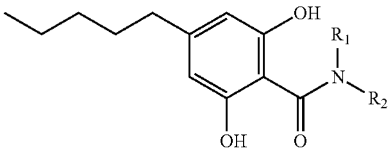

11

2,6-dihydroxy-4-pentylbenzoic acid (9)

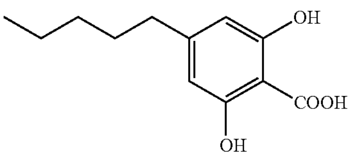 [SMILES: CCCCCc1cc(O)c(C(=O)O)c(O)c1]

The title product was synthesized via general procedure A using olivetol (3.0 g; 16.67 mmol). Purification was accomplished by CombiFlash chromatography using gradient ethyl acetate in hexanes to afford 1.75 g of a white solid (47% yield). $^1$H NMR (300 MHz, $d_6$, DMSO) δ0.82-0.87 (m, 3H), 1.22-1.32 (m, 4H), 1.41-1.51 (m, 2H), 2.41 (t, J=7.4 Hz, 2H), 6.16 (s, 2H), 11.4 (br s, 3H); MS (M+H$^+$) m/z: 225.2 (100%).

2,6-dihydroxy-4-pentyl-N-phenylbenzamide (11)

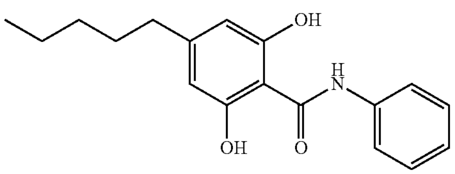 [SMILES: CCCCCc1cc(O)c(C(=O)Nc2ccccc2)c(O)c1]

The title product was synthesized via general procedure B using 2,6-dihydroxy-4-pentylbenzoic acid chloride (500 mg, 2.23 mmol), aniline (0.22 mL, 2.45 mmol) and TEA (0.9 mL, 2.67 mmol) at 0° C. and under a nitrogen atmosphere. The crude product was purified using normal phase flash chromatography to yield the title product as a red powder (334 mg, 50% yield). $^1$H NMR (300 MHz, $d_6$, DMSO) δ0.82-0.87 (m, 3H), 1.22-1.32 (m, 4H), 1.41-1.51 (m, 2H), 2.42 (t, J=7.4 Hz, 2H), 6.25 (s, 2H), 7.13 (t, J=7.7 Hz, 1H), 7.35 (t, J=7.3 Hz, 2H), 7.60 (d, J=7.3 Hz, 2H), 10.68 (s, 1H), 12.32 (s, 2H); MS (M+H$^+$) m/z: 300.1 (100%).

Scheme-3

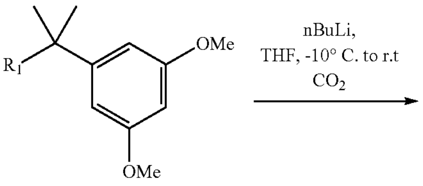

13

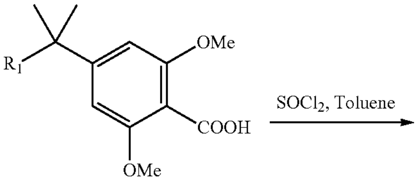

14

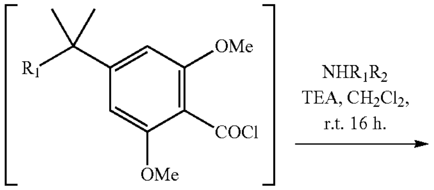

15

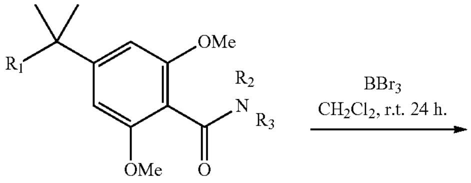

16

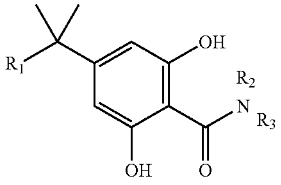

17

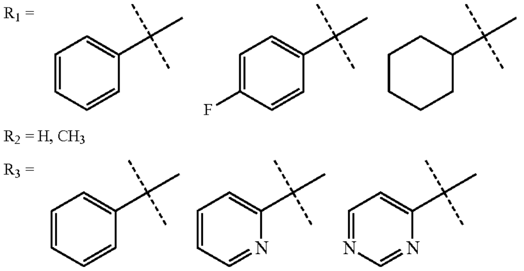

2,6-dimethoxy-4-(2-phenylpropan-2-yl)benzoic acid (14A)

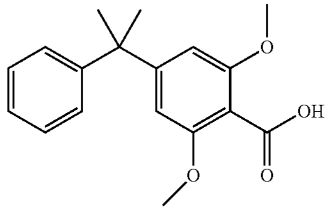 [SMILES: COc1cc(C(C)(C)c2ccccc2)cc(OC)c1C(=O)O]

The title product was prepared via general procedure A to afford the title product as a white solid. $^1$H NMR (300 MHz, $CDCl_3$) δ1.67 (s, 6H), 3.80 (s, 6H), 6.46 (s, 2H), 7.19-7.30 (m, 5H), MS ($M+H^+$) m/z: 301 (100%).

4-(2-(4-fluorophenyl)propan-2-yl)-2,6-dimethoxy-benzoic acid (14B)

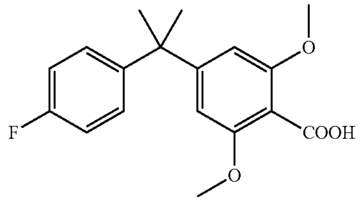 [SMILES: COc1cc(C(C)(C)c2ccc(F)cc2)cc(OC)c1C(=O)O]

The title product was prepared via general procedure A to produce the title product as a white solid. $^1$H NMR (300 MHz, $d_6$, DMSO) δ1.65 (s, 6H), 3.67 (s, 6H), 6.47 (s, 2H), 7.06 (t, J=8.8 Hz, 2H), 7.13-7.29 (m, 2H); MS ($M+H^+$) m/z: 319.2 (100%).

4-(2-cyclohexylpropan-2-yl)-2,6-dimethoxybenzoic acid (14C)

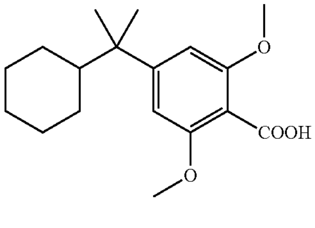 [SMILES: COc1cc(C(C)(C)C2CCCCC2)cc(OC)c1C(=O)O]

The title product was prepared via general procedure A to afford the title product as a white solid. $^1$H NMR (300 MHz, $CDCl_3$) δ0.99-1.89 (m, 17H), 3.71 (s, 6H), 6.55 (s, 2H), 12.34 (s, 1H), MS ($M+H^+$) m/z: 307(100%).

N-cyclohexyl-2,6-dimethoxy-4-(2-phenylpropan-2-yl)benzamide(16A)

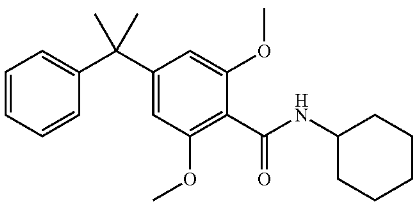 [SMILES: COc1cc(C(C)(C)c2ccccc2)cc(OC)c1C(=O)NC1CCCCC1]

The title product was synthesized via general procedure B using an acid chloride intermediate (250 mg, 0.78 mmol) and cyclohexanamine (0.43 g, 4.3 mmol). After completion of reaction, the solvent was removed under vacuum and the resulting residue was dissolved in ethyl acetate and washed with dilute HCl (5%) and water. The ethyl acetate layer was dried over sodium sulfate, and ethyl acetate was removed under vacuum. The resulting residue was used directly in the next step.

2,6-dimethoxy-N-phenyl-4-(2-phenylpropan-2-yl) benzamide (16B)

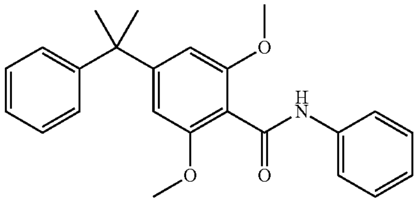 [SMILES: COc1cc(C(C)(C)c2ccccc2)cc(OC)c1C(=O)Nc1ccccc1]

The title product was synthesized via general procedure B using an acid chloride intermediate (250 mg, 0.78 mmol), and aniline (0.43 g, 5.3 mmol). After completion of reaction, the solvent was removed under vacuum and the resulting residue was dissolved in ethyl acetate and washed with dilute HCl (5%) and water. The ethyl acetate layer was dried over sodium sulfate, and ethyl acetate was removed under vacuum. The resulting crude residue was purified over column chromatography using gradient ethyl acetate in hexanes. $^1$H NMR (300 MHz, $d_6$, DMSO) δ1.68 (s, 6H), 3.67 (s. 6H), 6.52 (s, 2H), 7.02-7.31 (m, 8H), 7.70 (d, 2H) and 10.17 (s, 1H). MS ($M+H^+$) m/z: 376.1 (100%).

4-(2-cyclohexylpropan-2-yl)-2,6-dimethoxy-N-phenylbenzamide (16C)

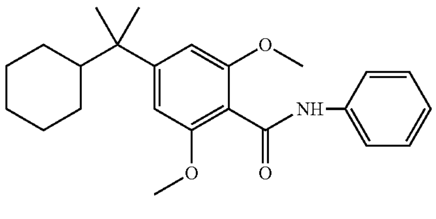 [SMILES: COc1cc(C(C)(C)C2CCCCC2)cc(OC)c1C(=O)Nc1ccccc1]

The title product was synthesized via general procedure B using intermediate acid chloride (250 mg, 0.78 mmol), and aniline (0.34 mL, 3.70 mmol). The title product was isolated as a sticky yellow solid (337 mg, 46.2% yield). $^{1}H$ NMR (300 MHz, $CDCl_3$) δ0.84-1.73 (m, 17H), 3.83 (s, 6H), 6.53 (s, 2H), 7.09 (t, J=7.6 Hz, 1H), 7.24 (s, 1H), 7.33 (t, J=7.7 Hz, 1H), 7.64 (d, J=6.0 Hz, 2H); MS (M+H) m/z: 382 (100%).

4-(2-cyclohexylpropan-2-yl)-2,6-dimethoxy-N-(pyridin-2-yl)benzamide (16D)

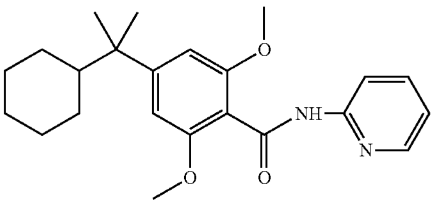 [SMILES: COc1cc(C(C)(C)C2CCCCC2)cc(OC)c1C(=O)Nc1ccccn1]

The title product was synthesized via general procedure B using an acid chloride intermediate and 2-aminopyridine (434.8 mg, 4.62 mmol). The title product was isolated as an off-white solid (120 mg, 60% yield). $^{1}H$ NMR (300 MHz, $CDCl_3$) δ0.89-1.71 (m, 17H), 3.75 (s, 6H), 6.45 (s, 2H), 6.82-6.86 (m, 1H), 7.66 (t, J=7.1 Hz, 1H), 7.75 (d, J=6.1 Hz, 1H), 8.44 (d, J=10.7 Hz, 1H), 9.69 (s, 1H); MS ($M+H^+$) m/z: 383 (100%).

4-(2-(4-fluorophenyl)propan-2-yl)-2,6-dimethoxy-N-phenylbenzamide (16F)

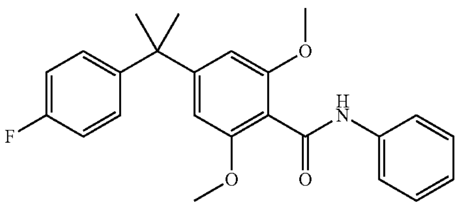 [SMILES: COc1cc(C(C)(C)c2ccc(F)cc2)cc(OC)c1C(=O)Nc1ccccc1]

The title product was synthesized via general procedure B using an acid chloride intermediate and aniline. The crude product was purified by CombiFlash using a gradient of 0-100% Hexanes and an EtOAc solvent system to afford the title product as an off-white solid (198 mg, Yield 51%). $^{1}H$ NMR (300 MHz, $d_6$, DMSO) δ1.68 (s, 6H), 3.67 (s, 6H), 6.47 (s, 2H), 7.03 (t, J=8.8 Hz, 2H), 7.12 (t, J=9.1 Hz, 3H), 7.26-7.33 (m, 4H), 7.69 (d, J=8.0 Hz, 2H), 10.17 (s, 1H); MS ($M+H^+$) m/z: 394.4 (100%).

N-cyclohexyl-4-(2-(4-fluorophenyl)propan-2-yl)-2,6-dimethoxybenzamide (16G)

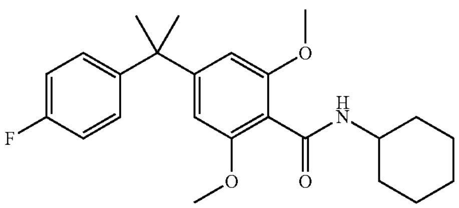 [SMILES: COc1cc(C(C)(C)c2ccc(F)cc2)cc(OC)c1C(=O)NC1CCCCC1]

The title product was synthesized via general procedure B using an acid chloride intermediate and cyclohexyl amine. The crude product was purified by CombiFlash using a gradient of 0-100% Hexanes and an EtOAc solvent system to afford the title product as an off white solid (175 mg, Yield 53%). $^{1}H$ NMR (300 MHz, $d_6$, DMSO) δ1.17-1.76 (m, 17H), 3.63 (s, 6H), 6.43 (s, 2H), 7.07-7.10 (m, 2H), 7.24-7.27 (m, 2H), 8.03 (d, J=7.9 Hz, 1H); MS ($M+H^+$) m/z: 400.8 (100%).

N-cyclohexyl-2,6-dihydroxy-4-(2-phenylpropan-2-yl)benzamide (17A)

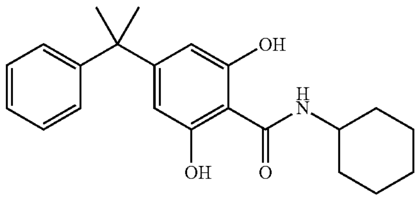 [SMILES: CC(C)(c1ccccc1)c1cc(O)c(C(=O)NC2CCCCC2)c(O)c1]

The title product was synthesized by general procedure C, using N-cyclohexyl-2,6-dimethoxy-4-(2-phenylpropan-2-yl)benzamide (340 mg, 0.89 mmol) and $BBr_3$ (0.84 mL, 8.9 mmol). The crude product was purified by CombiFlash using a gradient of 0-100% Hexanes and an EtOAc solvent system. The title produce was produced as a pale yellow gummy solid. (51 mg, 98%). $^{1}H$ NMR (300 MHz, $d_6$, DMSO) δ1.22-127 (m, 8H), 1.59 (s, 6H), 1.65-1.91 (m, 2H), 3.9 (m 1H), 6.26 (s, 2H), 7.29 (m, 5H), 8.15 (s, 1H),9.95 (s, 2H); MS ($M+H^+$) m/z: 354 (100%).

2,6-dihydroxy-N-phenyl-4-(2-phenylpropan-2-yl)benzamide (17B)

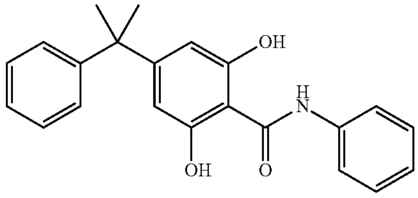 [SMILES: CC(C)(c1ccccc1)c1cc(O)c(C(=O)Nc2ccccc2)c(O)c1]

The title product was synthesized by general procedure C using 2,6-dimethoxy-N-phenyl-4-(2-phenylpropan-2-yl)benzamide. The crude product was purified by using a gradient of 0-100% Hexanes and an EtOAc solvent system. The title product was produced as a pale yellow gummy solid. (134 mg, 97%). $^{1}H$ NMR (300 MHz, $d_6$, DMSO) δ1.58 (s, 6H), 6.3 (s, 2H), 7.25-7.60 (m, 9H), 7.62 (d, J=8.52), 10.60 (s, 1H), 12.20 (s, 2H); MS ($M+H^+$) m/z: 348 (100%).

4-(2-cyclohexylpropan-2-yl)-2,6-dihydroxy-N-phenylbenzamide (17C)

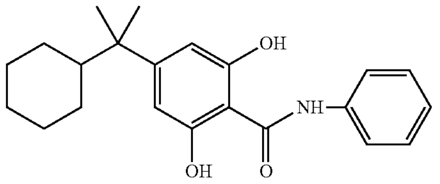 [SMILES: CC(C)(c1cc(O)c(C(=O)Nc2ccccc2)c(O)c1)C1CCCCC1]

The title product was synthesized by general procedure C using 4-(2-cyclohexylpropan-2-yl)-2,6-dimethoxy-N-phenylbenzamide (300 mg, 0.787 mmol) and $BBr_3$ (0.37 mL, 3.935 mmol. The crude product was purified with normal phase flash chromatography to yield the product as a white powder (145.9 mg, 99% purity, 86% yield). $^1$H NMR (300 MHz, $d_6$-DMSO) δ0.76-1.57 (m, 17H), 6.38 (s, 2H), 7.14 (t, J=12 Hz, 1H), 7.38 (t, J=7.4 Hz, 1H), 7.62 (d, J=7.7 Hz, 1H), 10.75 (s, 1H), 12.23 (s, 1H); MS (M+H$^+$) m/z: 354.2 (100%).

4-(2-cyclohexylpropan-2-yl)-2,6-dihydroxy-N-(pyridin-2-yl)benzamide (17D)

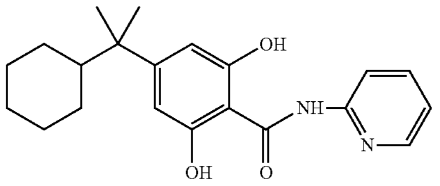 [SMILES: CC(C)(c1cc(O)c(C(=O)Nc2ccccn2)c(O)c1)C1CCCCC1]

The title product was synthesized by general procedure C using 4-(2-cyclohexylpropan-2-yl)-2,6-dimethoxy-N-(pyridin-2-yl)benzamide (100 mg, 0.26 mmol) and $BBr_3$ (0.13 mL, 1.31 mmol). The crude product was purified with normal phase flash chromatography to yield the title product as an off-white powder (70 mg mg, 98% purity, 70% yield). $^1$H NMR (300 MHz, $d_6$, DMSO) δ0.89-1.68 (m, 17H), 6.41 (s, 2H), 7.19 (t, J=3.0 Hz, 1H), 7.86 (t, J=3.0 Hz, 1H), 8.17 (d, J=6.3 Hz, 1H), 8.34-8.36 (m, 1H), 11.23 (s, 1H), 12.39 (s, 2H); MS (M+H$^+$) m/z: 355.5 (M+1).

4-(2-(4-fluorophenyl)propan-2-yl)-2,6-dihydroxy-N-phenylbenzamide (17F)

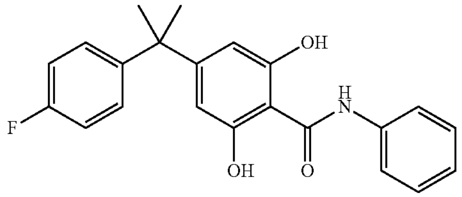 [SMILES: CC(C)(c1ccc(F)cc1)c1cc(O)c(C(=O)Nc2ccccc2)c(O)c1]

The title product was synthesized by general procedure C using 4-(2-(4-fluorophenyl)propan-2-yl)-2,6-dimethoxy-N-phenylbenzamide (150 mg, 0.38 mmol) and BBr 3 (0.18 mL, 1.9 mmol). The crude product was purified by CombiFlash using a gradient of hexanes and an EtOAc (0-100%) solvent system. The title product was isolated as a white solid (60 mg, Yield 54%). $^1$H NMR (300 MHz, $d_6$, DMSO) δ1.57 (s, 6H), 6.27 (s, 2H), 7.09-7.11 (m, 3H), 7.24-7.29 (m, 2H), 7.34-7.63 (m, 2H), 7.62 (d, J=7.7 Hz, 2H), 10.17 (s, 1H), 12.28 (s, 2H); MS (M+H$^+$) m/z: 367.4 (100%).

N-cyclohexyl-4-(2-(4-fluorophenyl)propan-2-yl)-2,6-dihydroxybenzamide (17G)

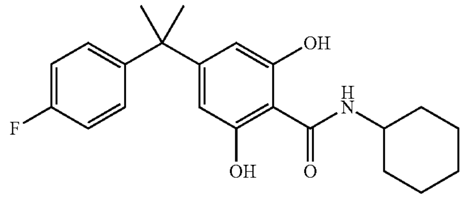 [SMILES: CC(C)(c1ccc(F)cc1)c1cc(O)c(C(=O)NC2CCCCC2)c(O)c1]

The title product was synthesized by general procedure C using N-cyclohexyl-4-(2-(4-fluorophenyl)propan-2-yl)-2,6-dimethoxybenzamide (150 mg, 0.37 mmol) and BBr 3 (0.19 mL, 1.9 mmol). The crude product was purified by CombiFlash using a gradient of hexanes and EtOAc (0-100%) solvent system to affod the title product as a white solid (50 mg, Yield 54%). $^1$H NMR (300 MHz, $d_6$, DMSO) δ1.31-1.34 (m, 6H), 1.54-1.85 (m, 11H), 6.19 (s, 2H), 7.07-7.10 (m, 2H), 7.21-7.26 (m, 2H), 8.71 (d, J=8.1 Hz, 1H)), 12.52 (s, 2H); MS (M+H$^+$) m/z: 378.4 (100%).

Scheme-4

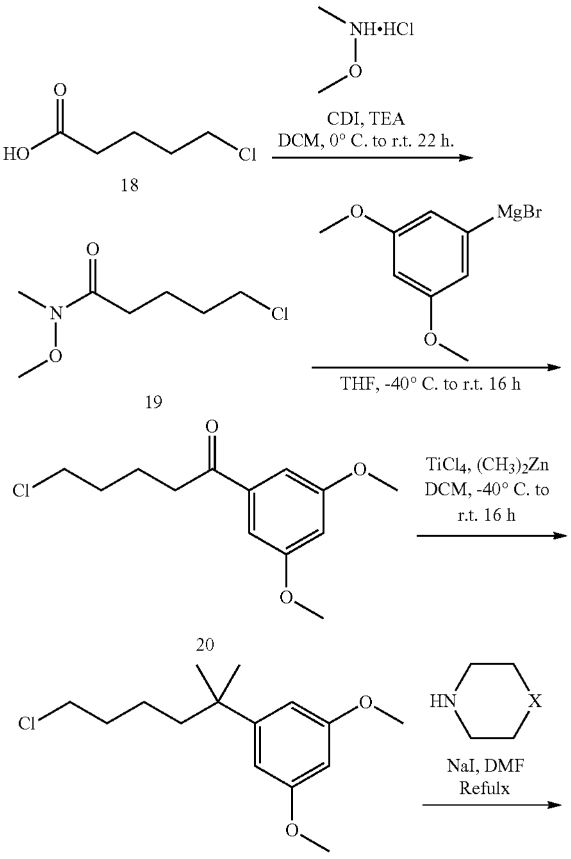

18

19

20

21

-continued

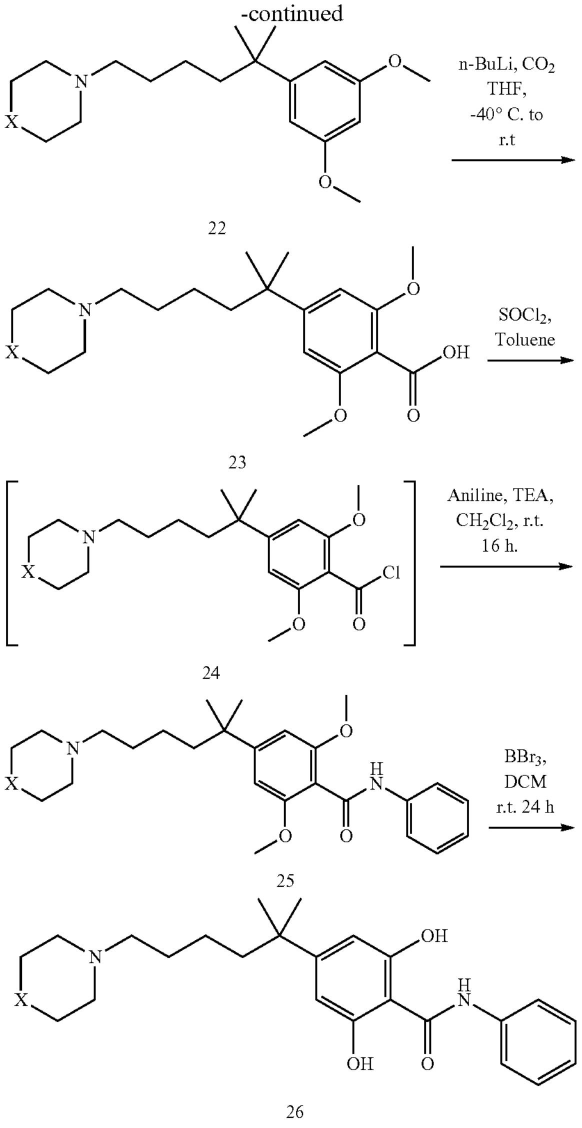

22, 23, 24, 25, 26

X = O, N—CH3

5-Chloro-N-methoxy-N-methylpentanamide (19)

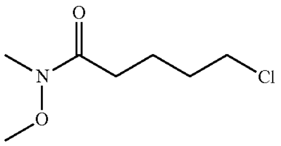

Carbonyldiimidazole (CDI) 6.53 g (40.26 mmol) was dissolved in 100 mL of dichloromethane in a round bottom flask. The reaction mixture was then cooled to 0° C. and 5-chloropentanoic acid 4.27 mL (36.6 mmol) was added dropwise, followed by the addition of triethyl amine (TEA) 5.58 mL (39.86 mmol). After stirring for 30 min, N,O-dimethylhydroxylamine hydrochloride 3.93 g (40.26 mmol) was added to the reaction mixture and the reaction was warmed to ambient temperature. The reaction was stirred for 22 h. Next day, the reaction was concentrated and extracted with ethyl acetate and $H_2O$. The organic layer was washed with 3M HCl (×3), brine (×2) and dried over anhydrous sodium sulfate $Na_2SO_4$. The pale brown product (6.87 g, quantitative yield) was directly used in next step without any purification. $^1H$ NMR (301 MHz, $CDCl_3$) δ3.67 (s, 3H), 3.55 (t, J=6.1 Hz, 2H), 3.17 (s, 3H), 2.45 (t, J=6.7 Hz, 2H), 1.86-1.72 (m, 4H).

5-Chloro-1-(3,5-dimethoxyphenyl)pentan-1-one (20)

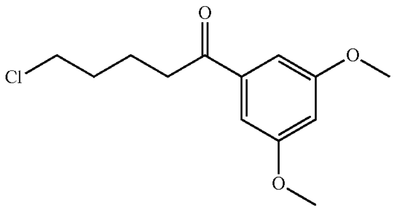 [SMILES: COc1cc(OC)cc(C(=O)CCCCCl)c1]

5-Chloro-N-methoxy-N-methylpentanamide 1.08 g (6.04 mmol) was dissolved in 20 mL of dry tetrahydrofuran and transferred to an oven dried 100 mL rb flask under nitrogen. The solution was cooled to −40° C. and (3,5-dimethoxyphenyl) magnesium bromide was added dropwise and warmed to ambient temperature overnight. Next day the reaction was quenched with an ammonium chloride ($NH_4Cl$) solution and extracted with EtOAc. The organic layer was washed with brine (×2) and dried over anhydrous $Na_2SO_4$. The crude was purified using a CombiFlash system (80 g regular column, flow rate: 40 mL/min, solvent: Hexane, EtOAc 0%-100%) to recover the title product as white crystals (0.84 g, 54% yield). $^1H$ NMR, (301 MHz, $CDCl_3$) δ7.08 (d, J=2.3 Hz, 2H), 6.71 (d, J=2.3 Hz, 1H), 6.65 (t, J=2.3 Hz, 1H), 3.83 (s, 6H), 3.58 (t, J=6.1 Hz, 2H), 2.97 (t, J=6.8 Hz, 2H), 1.88 (dd, J=6.3, 3.1 Hz, 4H). MS (M+H$^+$) m/z: 257.1 (100%).

1-(6-chloro-2-methylhexan-2-yl)-3,5-dimethoxybenzene (21)

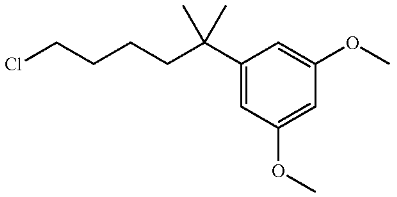 [SMILES: COc1cc(OC)cc(C(C)(C)CCCCCl)c1]

DCM (10 mL) was transferred to an oven dried three neck rb flask that was kept under a nitrogen atmosphere. Then flask was cooled to −40° C. and 19.56 mL (19.56 mmol) of a $TiCl_4$ solution (1M in toluene) was added, followed by rapid addition of a dimethyl zinc solution (1.2 M in toluene) 19.56 mL (19.56 mmol) via an addition funnel. The reaction was kept at −40° C. for 1 h and 0.84 g (3.26 mmol) of 5-chloro-1-(3,5-dimethoxyphenyl)pentan-1-one dissolved in DCM was added and stirred overnight. Next day the reaction was quenched with a cooled $NH_4Cl$ (aq) solution and the resulting product was extracted with four times with DCM. The combined organic phases were washed with brine (×2) and dried over anhydrous $Na_2SO_4$. The crude product was purified using a combi flash system (40 g regular column, flow rate: 40 mL/min, solvent: Hexane, EtOAc 0%-30%) to yield pale yellow product with 63% yield (0.56 g). $^1$H NMR (301 MHz, $CDCl_3$) δ6.47 (s, 2H), 6.30 (t, J=2.2 Hz, 1H), 3.79 (s, 6H), 3.45 (t, J=6.8 Hz, 2H), 1.73-1.53 (m, 6H), 1.27 (s, 6H). MS ($M+H^+$) m/z: 271.1 (100%).

General Procedure-D: Condensation of Morpholine or N-Methyl Piperzine with 1-(6-Chloro-2-Methylhexan-2-Yl)-3,5-Dimethoxybenzene One equivalent of 1-(6-chloro-2-methylhexan-2-yl)-3,5-dimethoxybenzene and morpholine or N-methylpiperzine and sodium iodide (NaI) was refluxed in dimethylformamide (DMF) at 80° C. for 4-5 h. The product was then extracted with EtOAc and the organic phase was washed with $H_2O$ (×5), brine (×2) and dried over anhydrous $Na_2SO_4$. The crude product was purified using a CombiFlash system (Solvent: 10% MeOH: DCM).

4-(5-(3,5-dimethoxyphenyl)-5-methylhexyl)morpholine (22A)

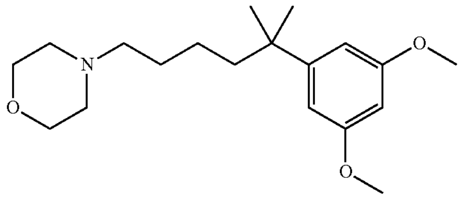 [SMILES: COc1cc(OC)cc(C(C)(C)CCCCN2CCOCC2)c1]

After purification, 0.96 g (87% yield) of the title product was isolated. $^1$H NMR (301 MHz, $CDCl_3$) δ6.47 (d, J=2.0 Hz, 2H), 6.29 (t, J=2.1 Hz, 1H), 3.79 (s, 6H), 3.68 (d, J=4.6 Hz, 4H), 2.38 (d, J=4.2 Hz, 4H), 2.27-2.19 (m, 2H), 1.57 (dd, J=11.4, 5.2 Hz, 3H), 1.38 (dd, J=15.5, 7.8 Hz, 2H), 1.25 (s, 6H), 1.14-1.00 (m, 2H). MS ($M+H^+$) m/z: 322.2 (100%).

1-(5-(3,5-dimethoxyphenyl)-5-methylhexyl)-4-methylpiperazine (22b)

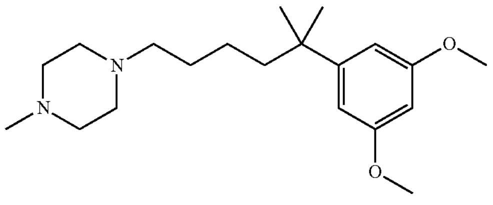

After purification, 0.6 g (67% yield) of the title product was isolated. $^1$H NMR (301 MHz, $CDCl_3$) δ6.46 (d, J=2.2 Hz, 2H), 6.29 (t, J=2.2 Hz, 1H), 3.78 (s, 6H), 2.48 (m, 8H), 2.31-2.27 (m, 4H), 1.56 (dd, J=10.4, 6.3 Hz, 2H), 1.41 (dt, J=15.5, 7.7 Hz, 2H), 1.24 (s, 6H), 1.13-0.97 (m, 2H). MS ($M+H^+$) m/z: 335.2 (100%).

2,6-dimethoxy-4-(2-methyl-6-morpholinohexan-2-yl)benzoic acid (23A)

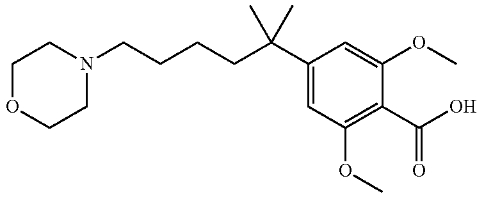 [SMILES: COc1cc(C(C)(C)CCCCN2CCOCC2)cc(OC)c1C(=O)O]

The title product was synthesized via general procedure-A using 4-(5-(3,5-dimethoxyphenyl)-5-methylhexyl)morpholine. After purification, 0.64 g (60% yield) of product was isolated. $^1$H NMR (301 MHz, DMSO-D6) δ3.70 (s, 6H), 3.54-3.47 (m, 2H), 2.26 (s, 4H), 2.22-2.13 (m, 2H), 1.57 (m, 2H), 1.33 (m, 2H), 1.24 (s, 6H), 1.02 (m, 2H). MS ($M+H^+$) m/z: 366.2 (100%).

2,6-dimethoxy-4-(2-methyl-6-(4-methylpiperazin-1-yl)hexan-2-yl)benzoic acid (23B)

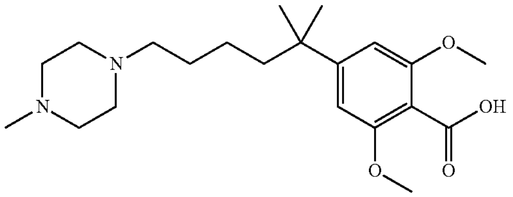 [SMILES: COc1cc(C(C)(C)CCCCN2CCN(C)CC2)cc(OC)c1C(=O)O]

The title product was synthesized via general procedure-A using 1-(5-(3,5-dimethoxyphenyl)-5-methylhexyl)-4-methylpiperazine. After purification, 0.48 g (70% yield) of title product was isolated. $^1$H NMR (301 MHz, DMSO-D6) δ3.65 (s, 6H), 3.34 (t, J=18.0 Hz, 4H), 2.26 (s, 4H), 2.19-2.13 (m, 2H), 2.11 (s, 3H), 1.57 (dd, J=10.3, 5.8 Hz, 2H), 1.31 (t, J=7.3 Hz, 2H), 1.22 (s, 6H), 1.02 (dd, J=16.9, 6.2 Hz, 2H). MS ($M+H^+$) m/z: 379.2 (100%).

General Procedure-E:

Acid amine coupling: An oven dried rb flask was fitted with 1 eq. of a compound, 2 eq. of hexafluorophosphate azabenzotriazole tetramethyl uronium (HATU), 3 eq. of N,N-diisopropylethylamine (DIPEA) with DMF and kept under nitrogen. After stirring for 15 min, 1.1 eq. of aniline was added. The reaction kept stirring at ambient temperature overnight. Next day, the reaction was quenched with $H_2O$ and the product was extracted with EtOAc. The organic layer was washed with brine (×2) and dried over anhydrous $Na_2SO_4$. The title product was purified using a CombiFlash system (10% MeOH: DCM).

2,6-Dimethoxy-4-(2-methyl-6-morpholinohexan-2-yl)-N-phenylbenzamide (25A)

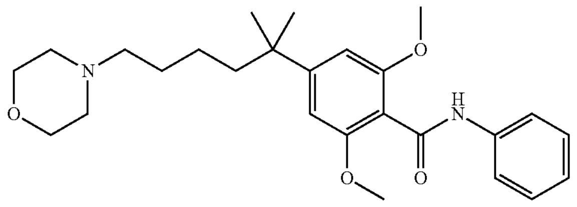 [SMILES: COc1cc(C(C)(C)CCCCN2CCOCC2)cc(OC)c1C(=O)Nc1ccccc1]

The title product was synthesized via general procedure-E using 2,6-dimethoxy-4-(2-methyl-6-morpholinohexan-2-yl) benzoic acid and aniline. After purification, 0.35 g (58% yield) of the title product was isolated. $^{1}H$ NMR (301 MHz, $CDCl_3$) δ7.64 (d, J=7.8 Hz, 2H), 7.48 (t, J=1H), 7.36-7.26 (m, 2H), 7.12 (d, J=7.5 Hz, 1H), 6.54 (s, 2H), 3.83 (s, 6H), 3.73-3.63 (m, 4H), 2.40 (s, 4H), 2.31-2.13 (m, 2H), 1.62 (d, J=16.6 Hz, 2H), 1.41 (s, 2H), 1.30 (s, 6H), 1.08 (s, 2H). MS $(M+H^+)$ m/z: 441.2 (100%).

2,6-dimethoxy-4-(2-methyl-6-(4-methylpiperazin-1-yl)hexan-2-yl)-N-phenylbenzamide (25B)

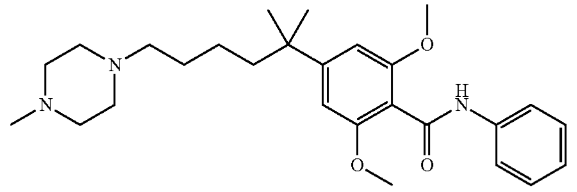 [SMILES: COc1cc(C(C)(C)CCCCN2CCN(C)CC2)cc(OC)c1C(=O)Nc1ccccc1]

The title product was synthesized via general procedure-E using 2,6-dimethoxy-4-(2-methyl-6-(4-methylpiperazin-1-yl)hexan-2-yl)benzoic acid and aniline. After purification, 0.22 g (47% yield) of the title product was isolated. $^{1}H$ NMR (301 MHz, $CDCl_3$) δ7.77 (s, 1H), 7.61 (d, J=8.0 Hz, 2H), 7.34 (t, J=7.8 Hz, 2H), 7.13 (t, J=7.3 Hz, 1H), 4.29 (s, 1H), 3.83 (s, 6H), 2.69 (t, J=16.4 Hz, 7H), 2.56-2.45 (m, 2H), 2.37 (s, 3H), 1.68-1.55 (m, 2H), 1.43 (s, 2H), 1.29 (s, 5H), 1.00 (s, 2H). MS $(M+H^+)$ m/z: 454.3 (100%).

2,6-dihydroxy-4-(2-methyl-6-morpholinohexan-2-yl)-N-phenylbenzamide (26A)

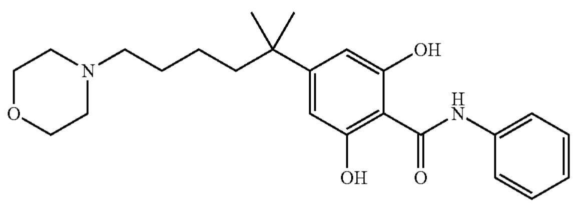 [SMILES: CC(C)(CCCCN1CCOCC1)c1cc(O)c(C(=O)Nc2ccccc2)c(O)c1]

The title product was synthesized via general procedure C using 2,6-dimethoxy-4-(2-methyl-6-morpholinohexan-2-yl)-N-phenylbenzamide. Yield 51 mg. $^{1}H$ NMR (301 MHz, $CD_3OD$) δ7.62 (d, J=8.5 Hz, 2H), 7.36 (t, J=7.1 Hz, 2H), 7.15 (t, J=7.9 Hz, 1H), 6.46 (s, 2H), 3.88 (s, 4H), 3.22 (s, 4H), 3.02 (t, J=10.6 Hz, 3H), 1.65 (d, J=9.9 Hz, 4H), 1.28 (s, 6H), 1.23-1.11 (m, 2H). MS (M+1-1") m/z: 413.2 (100%).

2,6-dihydroxy-4-(2-methyl-6-(4-methylpiperazin-1-yl)hexan-2-yl)-N-phenylbenzamide (26B)

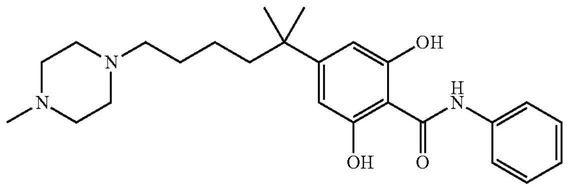 [SMILES: CN1CCN(CCCCC(C)(C)c2cc(O)c(C(=O)Nc3ccccc3)c(O)c2)CC1]

The title product was synthesized via general procedure C using 2,6-dimethoxy-4-(2-methyl-6-(4-methylpiperazin-1-yl)hexan-2-yl)-Ar-phenylbenzamide. Yield 3 mg. $^{1}H$ NMR (301 MHz, $CD_3OD$) δ7.61 (d, J=8.5 Hz, 2H), 7.36 (t, J=8.0 Hz, 2H), 7.15 (t, J=7.9 Hz, 1H), 6.45 (s, 2H), 3.14 (m, 8H), 2.86-2.78 (m, 2H), 2.73 (s, 3H), 1.69-1.61 (m, 2H), 1.56 (dd, J=14.2, 6.5 Hz, 2H), 1.27 (s, 6H), 1.16 (m, 2H). MS $(M+H^+)$ m/z: 426.2 (100%).

Effects of Compound-5B on proliferation in breast cancer cells: Using the CellTiter-GLo viability/proliferation assay and MDA-MB231 cells, the percent of cell growth inhibited by different doses of Compound-5B was assessed as shown in Table 1. Cell proliferation of MDA-MB231 cells in the presence of multiple drugs was measured using the CellTiter-Glo luminescent Assay over a two-day treatment period and $IC_{50}$ values were calculated (Table 1). The $IC_{50}$ and corresponding 95% confidence limits (CL) were calculated using non-linear regression analysis.

TABLE 1
Cellular inhibition data for compounds in breast cancer cells
| S.N. | Structure | Compound number | Inhibition of MDA-MB231 D3H |
|---|---|---|---|
| 1 | 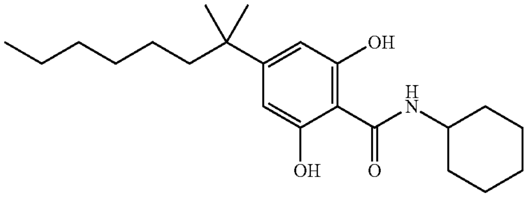 [SMILES: CCCCCCC(C)(C)c1cc(O)c(C(=O)NC2CCCCC2)c(O)c1] | 5A | I |
| 2 | 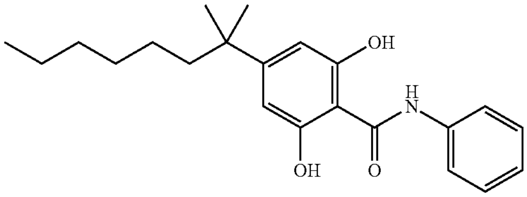 | 5B | I |
| 3 | 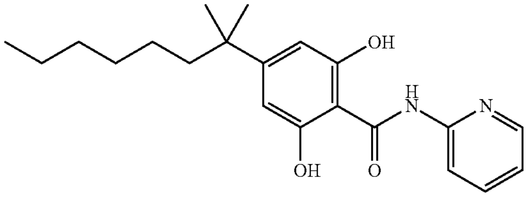 | 5C | I |
| 4 | 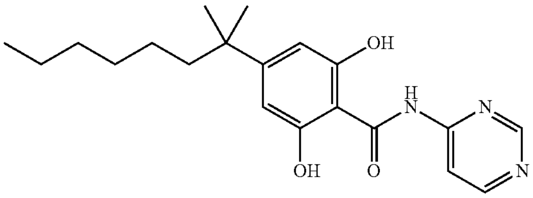 [SMILES: CCCCCCC(C)(C)c1cc(O)c(C(=O)Nc2ccncn2)c(O)c1] | 5D | I |
| 5 | 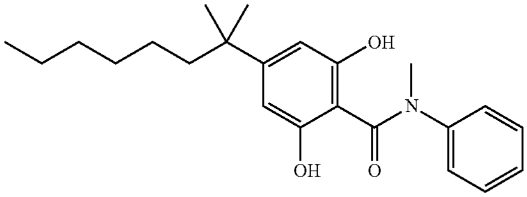 | 5E | III |
| 6 | 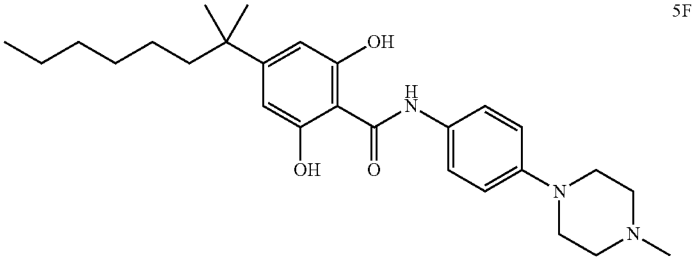 | 5F | V |
| 7 | 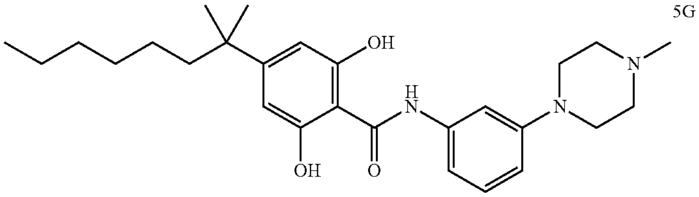 | 5G | III |

TABLE 1-continued
| Cellular inhibition data for compounds in breast cancer cells | | | |
|---|---|---|---|
| S.N. | Structure | Compound number | Inhibition of MDA-MB231 D3H |
| 8 | 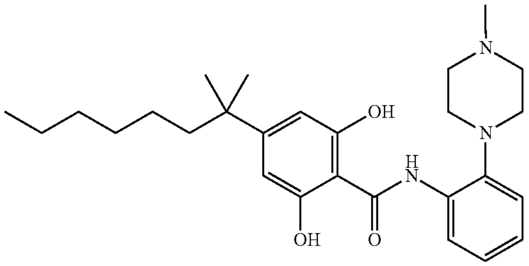 [SMILES: CCCCCCC(C)(C)c1cc(O)c(C(=O)Nc2ccccc2N2CCN(C)CC2)c(O)c1] | 5H | II |
| 9 | 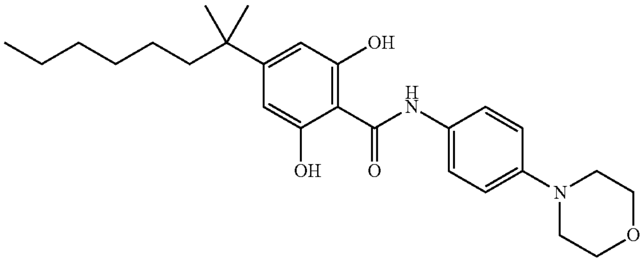 [SMILES: CCCCCCC(C)(C)c1cc(O)c(C(=O)Nc2ccc(N3CCOCC3)cc2)c(O)c1] | 5I | I |
| 10 | 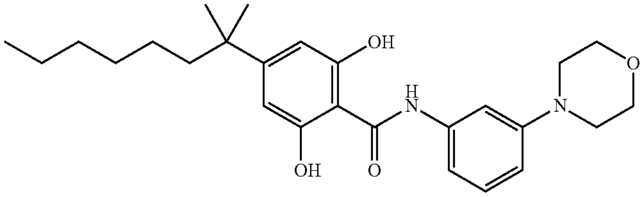 [SMILES: CCCCCCC(C)(C)c1cc(O)c(C(=O)Nc2cccc(N3CCOCC3)c2)c(O)c1] | 5J | I |
| 11 | 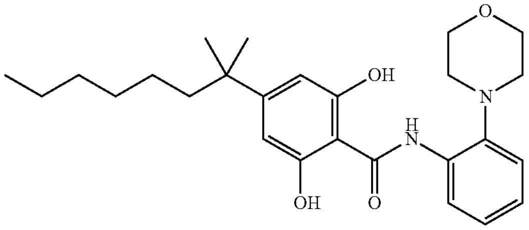 [SMILES: CCCCCCC(C)(C)c1cc(O)c(C(=O)Nc2ccccc2N2CCOCC2)c(O)c1] | 5K | I |
| 12 | 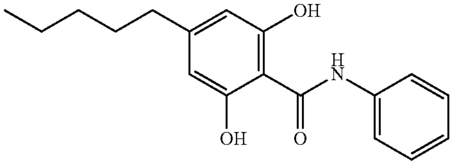 [SMILES: CCCCCc1cc(O)c(C(=O)Nc2ccccc2)c(O)c1] | 11 | I |
| 13 | 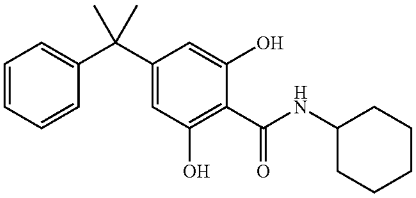 [SMILES: CC(C)(c1ccccc1)c1cc(O)c(C(=O)NC2CCCCC2)c(O)c1] | 17A | II |

TABLE 1-continued

Cellular inhibition data for compounds in breast cancer cells

| S.N. | Structure | Compound number | Inhibition of MDA-MB231 D3H |
|---|---|---|---|
| 14 | 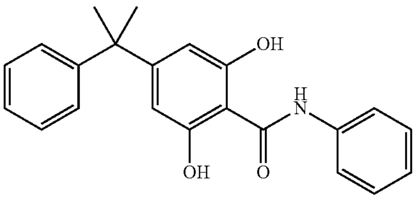 [SMILES: CC(C)(c1ccccc1)c1cc(O)c(C(=O)Nc2ccccc2)c(O)c1] | 17B | I |
| 15 | 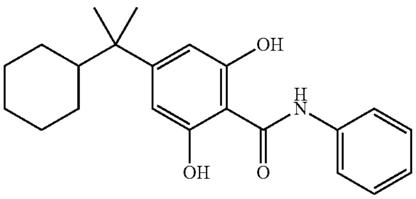 [SMILES: CC(C)(c1cc(O)c(C(=O)Nc2ccccc2)c(O)c1)C1CCCCC1] | 17C | I |
| 16 | 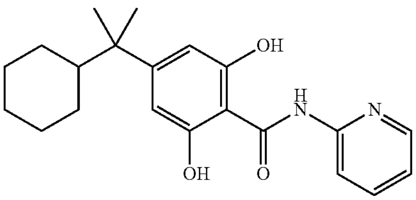 [SMILES: CC(C)(c1cc(O)c(C(=O)Nc2ccccn2)c(O)c1)C1CCCCC1] | 17D | I |
| 17 | 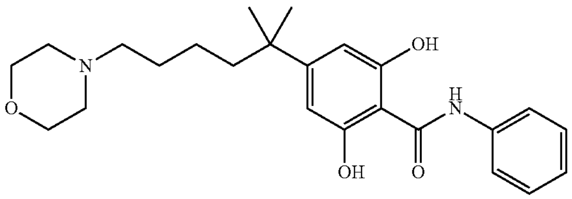 [SMILES: CC(C)(CCCCN1CCOCC1)c1cc(O)c(C(=O)Nc2ccccc2)c(O)c1] | 26A | III |

I = $IC_{50}$: <500 nM
II = $IC_{50}$: 500 nM to 1 μM
III = $IC_{50}$: 1 μM to 5 μM
IV = $IC_{50}$: 5 μM to 15 μM and
V = No effect.

Evaluating ADME of Compound-5B in vitro. It is important to evaluate ADME first in culture as it allows for the selection of the best candidate for PK analysis in vivo. ADME analysis of Compound-5B was performed by Eurofins.

Compound-5B has low aqueous solubility, good stability in mouse liver microsomes, high plasma protein binding, and no inhibition of the essential cardiac channel hERG. Compound-5B does not inhibit the important CYP450 isoforms at 1 μM. However, some inhibition was found for CYP2C8 and CYP2C9 at 10 μM. Microsomal stability assays suggested acceptable clearance and half-life for Compound-5B.

The fundamental pharmacokinetic parameters of Compound-5B through IV were evaluated at a 1 mpk dose. Compound-5B exhibited low clearance, acceptable half-life and good exposure. Identification of off-target interactions at the earliest stage of drug discovery has proven to be a cost effective and efficient process to managing candidate selection. Eurofin's Kinome scan assay was used to screen Compound-5B against 468 kinases at 1 μM and 10 μM concentrations. No significant inhibition was found. In order to understand any potential pharmacological cross reactivity, a known contributor to clinical adverse drug reactions Compound-5B was tested in SAFETY scan E/$IC_{50}$ ELECT. This is a highly standardized assay and more details about it can be found at Eurofin's website. Among 78 SAFETY scan assays, Compound-5B showed mild inhibition against ADRB1, ADRB2 (β-Adrenergic receptor), DRD1 (Dopamine receptor D1) and HRH2 (Histamine receptor) which are GPCR targets between 0.64 μM to 0.75 μM. Compound-5B does not bind to the cannabinoid receptors.

Effects of Compound-5B on breast cancer cell proliferation, Id-1 expression and invasion in culture. Compound-5B has significant potency for inhibition of Id-1 expression in MDA-MB231 cells (FIG. 1A) and primary patient-derived BRC25 cells (FIG. 1B) and proliferation in mouse 4T1 TNBC ($IC_{50}$=group II for inhibition of cell proliferation) and human MDA-MB231 (Table 1). It also inhibits the invasion of MDA-MB231 cells (FIG. 1C). The ability of the cells to migrate and invade in modified Boyden chambers was determined. The percentage relative invasion was calculated as the effect on treated cells/vehicle cells×100. Respective controls (vehicle treated cells) were set as 100%.

Effects of the combination of paclitaxel and Compound-5B on breast cancer cell proliferation. FIG. 2 presents data showing the effects of Compound-5B (FIG. 2A) and paclitaxel (FIG. 2B) on breast cancer cell viability alone and in combination (FIG. 2C).

FIG. 3 demonstrates that at optimal combined ratios, Compound-5B can enhance the ability of paclitaxel to inhibit the viability of MDA-MB231 breast cancer cells. Concentration-response curves were generated for Compound-5B and paclitaxel alone and in combination (FIG. 2C). The inhibitory values from the concentration response curves were used to calculate combination index (CI) values at multiple combination ratios (FIG. 3A). Methods: Multiple viability assays in a 384 well format were run for each compound and the average percent inhibition of cell viability was calculated and transformed to fraction affected (Fa) e.g., percent inhibitory effect. CI values were calculated using Compusyn software (FIG. 3B). After determining the ($IC_{50}$/Fa 0.5) values of the drugs individually (C), components were then combined at specific concentration ranges (FIG. 3B) and a combination index was calculated where CI<1, =1, and >1 indicate synergism, additive effect, and antagonism, respectively.

Figure 4B:
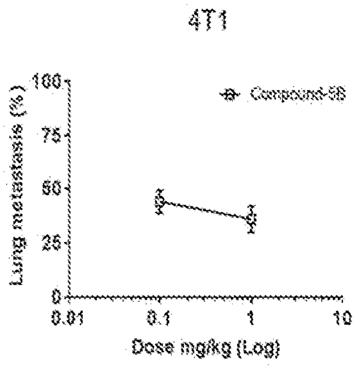
Figure 4C:
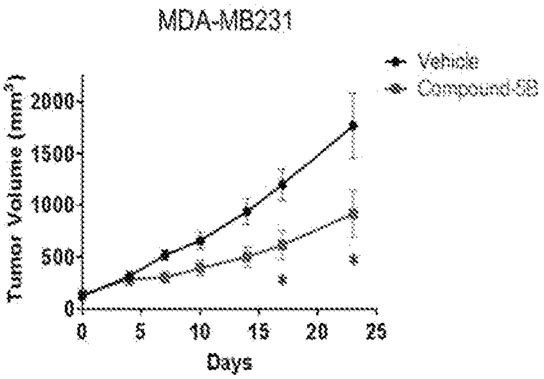

Antitumor activity of Compound-5B in vivo in breast cancer. Based on the activity of Compound-5B in culture, the antitumor activity of Compound-5B was tested in vivo in two models of breast cancer (FIG. 4). Compound-5B produced a potent inhibition of Id-1 expression in human MDA-MB231 cells (FIG. 1A). We also determined whether it produced a similar effect in mouse 4T1 breast cancer cells. This cell line is commonly used for seeding a lung metastatic model in mice. It was determined that Compound-5B produce downregulation of Id-1 protein expression. LC=loading control (FIG. 4A). FIG. 4 demonstrates that Compound-5B inhibits breast cancer metastasis and primary tumor growth in mouse models of TNBC. Lung metastases were generated in BALB/c mice by tail vein injection of $4\times10^4$ 4T1 cells. Two days after the injection, the tumor bearing mice were injected i.p. once a day, six days a week, with vehicle or Compound 5B three weeks. Lung metastasis % (total metastatic foci in treated/vehicle×100) was evaluated (FIG. 4B). Compound-5B was also able to inhibit primary tumor growth (FIG. 4C). Primary tumors were generated in athymic nu/nu mice after mammary fat pad injection of $1\times10^4$ MDA-MB231 cells. Animals with established tumors (average volume of 100 $mm^3$) were randomized and treated once daily, 6 days a week, with i.p., injections of vehicle, or 1 mg/kg Compound-5B, tumors were measured once weekly by an operator blinded to the treatment groups. Changes in tumor volume ($mm^3$) were calculated as (length×width2)/2. *indicates statistically significant differences between vehicle and Compound-5B ($p<0.05$, Two-way ANOVA repeated measures, and Tukey's multiple comparisons test).

Effects of Compound-5B on proliferation and Id-1 expression in pancreatic cell lines. Compound-5B was next tested for inhibition of cell viability/proliferation in the three pancreatic cancer cell lines and two primary patient-derived cancer cell lines. Compound-5B inhibited cell viability/proliferation of all the cancer cell lines (Table 2). The culturing condition for the pancreatic cell lines was similar to those used in the breast cancer lines, with the exception of the primary patient-derived pancreatic cancer cell lines (PANC9 and PANC13). For determining inhibition of cell proliferation in patient-derived pancreatic cancer cells were cultured in a T75 ultra low attachment flasks with DMEM/F12 media supplemented with B27, penicillin/streptomycin (10,000 u/mL), 50 □g/mL human epidermal growth factor (hEGF), 50 µg/mL human fibroblast growth factor, and 5 µg/mL heparin. Cells were plated in a 384-well plate and incubated for three days to promote the formation of tumorspheres. Cells were then treated with Compound-5B for three days. Cell proliferation of pancreatic cells in the presence of drug was measured using the CellTiter-Glo luminescent Assay and $IC_{50}$ values were calculated (Table 2). The $IC_{50}$ and corresponding 95% confidence limits (CL) were calculated using non-linear regression analysis.

TABLE 2

Cellular inhibition data for key compounds in pancreatic cancer cell lines

| S.N. | Structure | Compound number | Cancer cell line | $IC_{50}$ category |
|---|---|---|---|---|
| 2 | 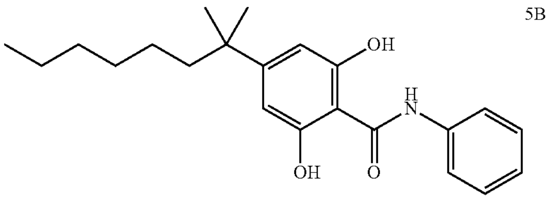 | 5B | PANC-1 | I |
| 2 | 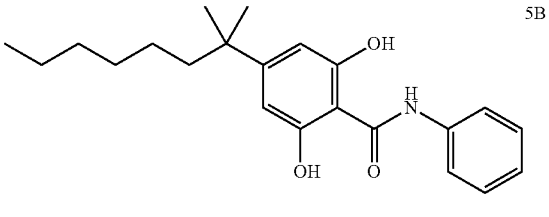 | 5B | BXPC-3 | III |

TABLE 2-continued

Cellular inhibition data for key compounds in pancreatic cancer cell lines

| S.N. | Structure | Compound number | Cancer cell line | $IC_{50}$ category |
|---|---|---|---|---|
| 2 | 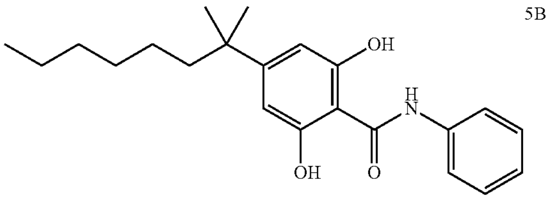 | 5B | SW1990 | I |
| 2 | 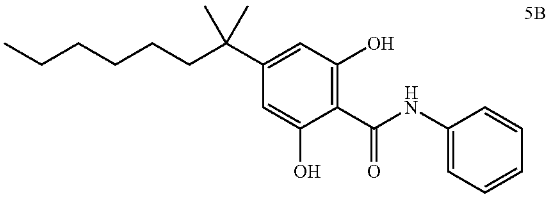 | 5B | PANC9 | I |
| 2 | 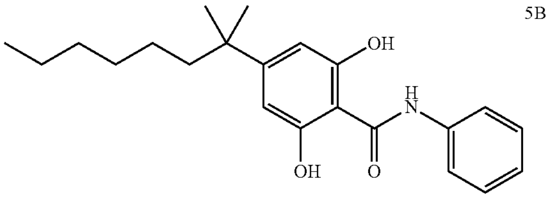 | 5B | PANC13 | I |

I = $IC_{50}$: <500 nM
II = $IC_{50}$: 500 nM to 1 μM
III = $IC_{50}$: 1 μM to 5 μM

Figure 5A:
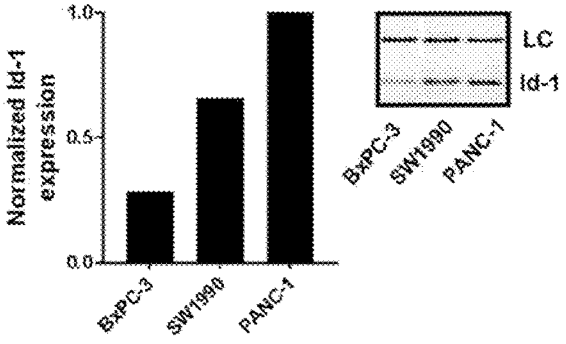
FIG. 5A-B shows that Compound-5B was most effective at inhibiting cell viability/proliferation in the pancreatic cancer cell lines expressing the highest level of Id-1 expression, PANC-1 (FIG. 5A). Effects of Compound-5B on Id-1 expression: Compound-5B was tested for its ability to reduce Id-1 expression in PANC-1 cancer cells using Western analysis (FIG. 5B). Compound-5B was able to effectively inhibit Id-1 expression in PANC-1 cells.

The expression of Id-1 was first assessed in progressively more undifferentiated and aggressive pancreatic cell lines (e.g., see FIG. 5A). The order of the three cell lines was BxPC-3→SW1990→PANC-1; the most differentiated being BxPC-3, and the most aggressive being PANC-1. The expression of Id-1 increased as the aggressiveness of the tumor cells increased, which was in agreement with past reports in other cancer types. Compound-5B was most effective at inhibiting cell viability/proliferation in the pancreatic cancer cell lines expressing the highest level of Id-1 expression, PANC-1 (FIG. 5A). The $IC_{50}$ for Compound-5B demonstrated a 38-fold improvement in potency compared to the original parent compound, CBD ($IC_{50}$=1.9 μM).

Figure 5B:
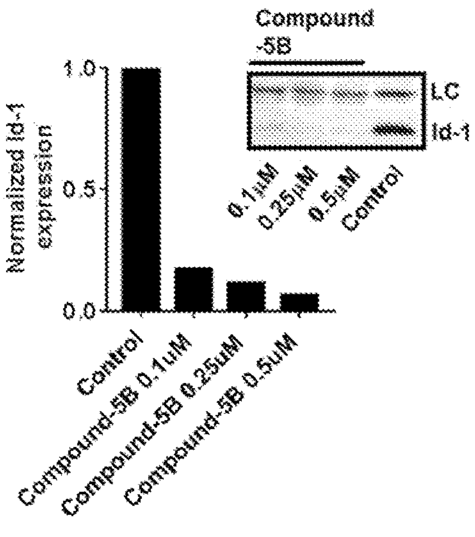

Effects of Compound-5B on Id-1 expression: Compound-5B was tested for its ability to reduce Id-1 expression in PANC-1 cancer cells using Western analysis (FIG. 5B). Compound-5B was able to effectively inhibit Id-1 expression in PANC-1 cells.

Figure 6A:
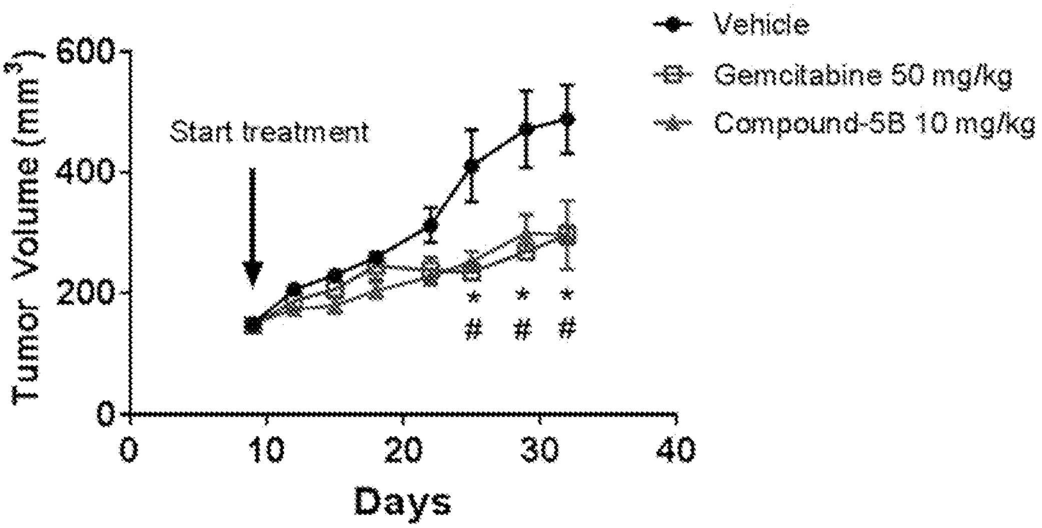
FIG. 6A-B shows the antitumor activity of Compound-5B in vivo in comparison to the first-line agent gemcitabine (e.g., see FIG. 6A). 10 mg/kg of Compound-5B reduced the growth of PANC-1 tumors as effectively as gemcitabine. Importantly, while the mice treated with a therapeutic dose of gemcitabine experienced significant weight loss, a metric of drug toxicity, there was no significant weight loss (FIG. 6B).

In addition, because of the significant potency of Compound-5B at targeting Id-1 expression and cancer cell aggressiveness in PANC-1 cells, the antitumor activity of Compound-5B was tested in vivo in comparison to the first-line agent gemcitabine (e.g., see (FIG. 6A). Tumors were generated in athymic nu/nu mice by subcutaneous injection of $1\times10^4$ PANC-1 cells. Animals with established tumors (average volume of 100 $mm^3$) were randomized and treated once daily with i.p. injections of vehicle, 10 mg/kg Compound-5B, or three times a week with i.p. injections of 50 mg/kg of gemcitabine until the completion of the study as shown in FIG. 6A. *indicates statistically significant differences between vehicle and Compound-5B ($p<0.05$, Two-way ANOVA repeated measures, and Tukey's multiple comparisons test).

Figure 6B:
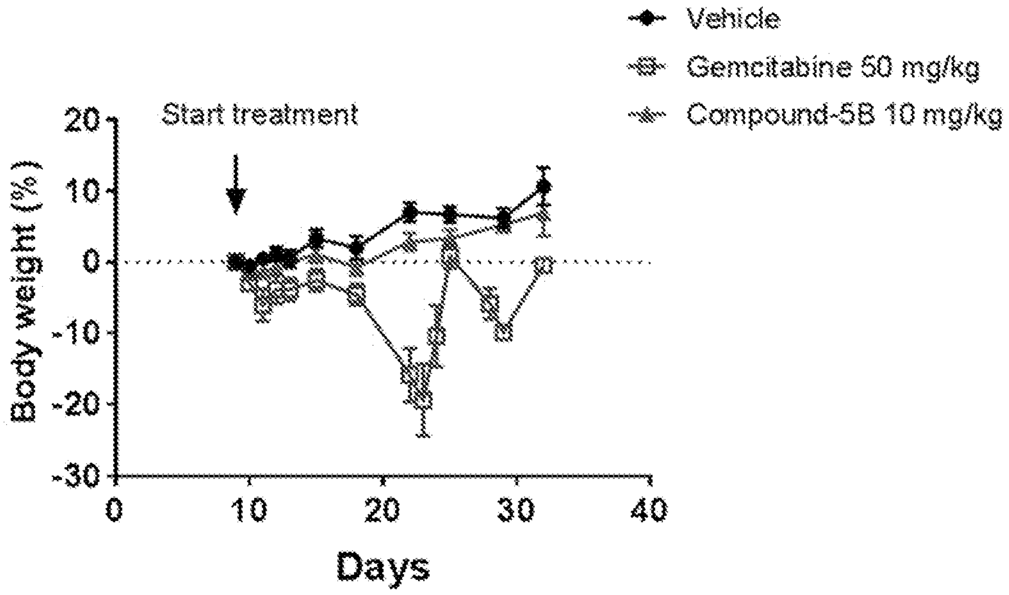

10 mg/kg of Compound-5B reduced the growth of PANC-1 tumors as effectively as gemcitabine. Importantly, while the mice treated with a therapeutic dose of gemcitabine experienced significant weight loss, a metric of drug toxicity, there was no significant weight loss (FIG. 6B). Thus, the data demonstrate that Compound-5B is highly active at inhibiting Id-1 expression, and pancreatic cancer cell aggressiveness both in culture and in vivo. Furthermore, Compound-5B is as efficacious as the standard-of-care gemcitabine, and most importantly it is significantly less toxic than the first-line agent, gemcitabine.

Optimization of dosing formulations for Compound-5B: Formulation conditions for optimal dosing of Compound-5B in mice was determined using in vivo PK evaluation. Suitable formulation conditions for in vivo studies in mice is determined and dose response IP PK is evaluated. A dosing vehicle and target dose concentration of Compound-5B suitable for 21-day repeat IP dosing in mice is determined. The solubility of Compound-5B LC-MS/MS estimation) is evaluated in up to 3 different dosing vehicles using the following formulation approaches: assess solubility with pH manipulation; assess solubility in co-solvents; assess solubility in liquid surfactants; assess solubility in non-aqueous systems and assess effects on solubility with complexing agents. The goal is to identify vehicle or mixture of vehicles that meet the target concentration. Estimation by LC-MS/MS analysis was used. Samples were analyzed by LC-MS/MS in triplicate (n=3) with a minimum 6-point standard curve to confirm concentration of Compound-5B. Once the vehicle(s) meet target concentration, precipitation potential was evaluated by diluting with aqueous media and visually evaluating particle formation or solubility.

The PK profiling was performed using male CD-1 mice. The route of administration for dosing was intraperitoneal i.p. (used in antitumor studies. The CD-1 mice were treated with Compound-5B using the optimized formulation via i.p. route of administration and one dose per route was tested. For statistical comparison and scientific rigor, 3 male mice per treatment group were used to complete the study. Pharmacokinetics were assessed from hemolyzed blood derived from a blood draw and analyzed using LC-MS/MS at specific time points. Mice were serially bled over a 24-hour period. Route of administration is intraperitoneal (IP). Dosing occurs once via the corresponding dose route. Animals were fasted prior to dosing with water being provided ad libitum. Blood was collected via the tail vein (~25 µL per blood draw), placed in tubes with anticoagulant and combined with an equal volume of water. After collection, hemolyzed blood was frozen at −80° C. Samples were transferred for analysis.

Pharmacokinetic parameters for each dose route AUC, half-life, Cmax, tmax and Mean residence time (MRT) were determined. The formulation demonstrating the optimum PK profile for Compound-5B was evaluated in preclinical mouse models of cancer.

Effects of Compound-5B on cell proliferation in additional cancer cells: To determine whether Compound-5B would have broad based anticancer activity, we study whether Compound-5B would be effective at inhibiting cell proliferation in a variety of cancers overexpressing Id-1. The assay conditions used were identical to those presented for breast and pancreatic cancers. Indeed, Compound-5B was potent at inhibiting cell proliferation in blood cancer (leukemia), glioblastoma, prostate, and ovarian cancer.

TABLE 3

Cellular inhibition data for Compound-5B across multiple cancers.

| S.N. | Structure | Compound number | Cancer cell line | $IC_{50}$ category |
|---|---|---|---|---|
| 2 | 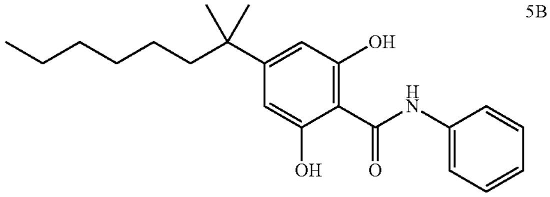 | 5B | Kasumi -1 (leukemia) | I |
| 2 | 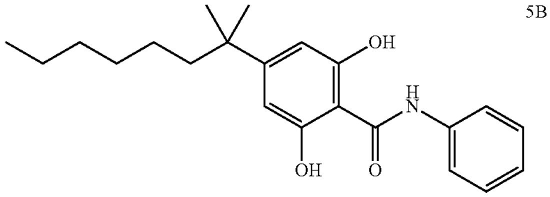 | 5B | U251 (glioblastoma) | I |
| 2 | 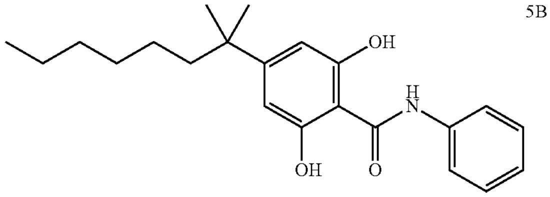 | 5B | DU145 (prostate) | I |
| 2 | 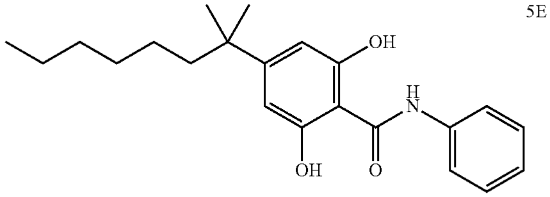 | 5E | SKOv3 (ovarian) | II |

I = $IC_{50}$: <500 nM

II = $IC_{50}$: 500 nM to 1 µM

III = $IC_{50}$: 1 µM to 5 µM

What is claimed is:

1. A resorcinol-based compound having the structure of:

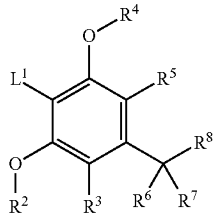

or a pharmaceutically acceptable salt, or prodrug thereof, wherein:

$L^1$ is

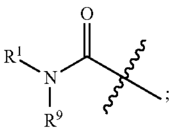;

$R^1$ is selected from

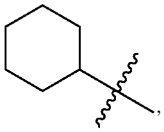, 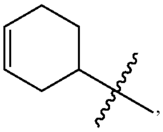, 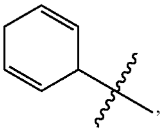,

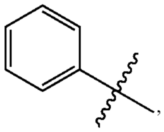, 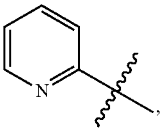, 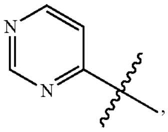,

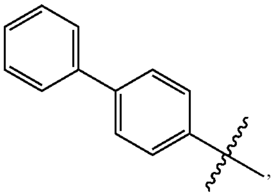, 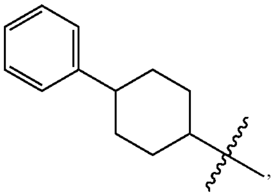,

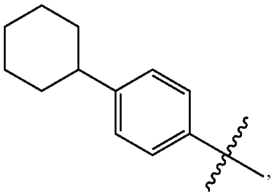, 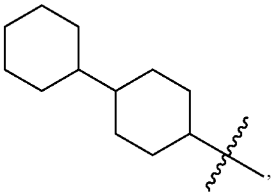,

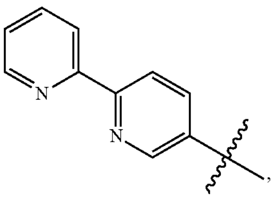,

-continued

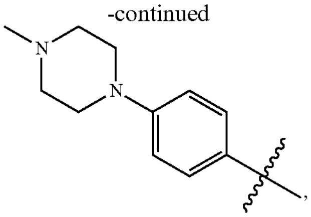,

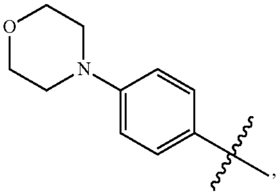, 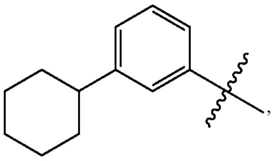,

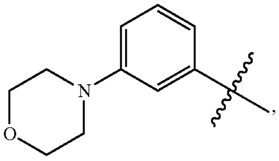,

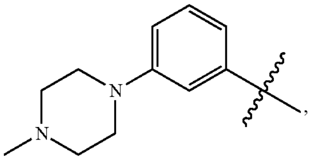, 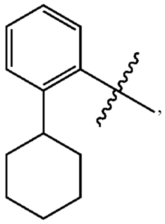,

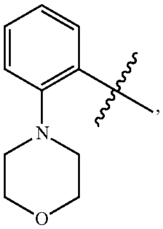, and 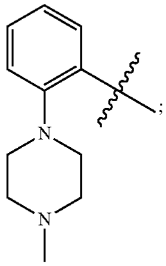;

$R^2$, $R^4$, $R^6$, and $R^7$ are each independently selected from H or a ($C_1$-$C_3$) alkyl;

$R^3$ and $R^5$ are each independently selected from H, hydroxyl, a ($C_1$-$C_3$) alkyl, and a halo;

$R^8$ is selected from an optionally substituted ($C_1$-$C_{12}$) alkyl, an optionally substituted ($C_1$-$C_{11}$) hetero-alkyl, an optionally substituted ($C_1$-$C_{12}$) alkenyl, an optionally substituted ($C_1$-$C_{11}$) hetero-alkenyl, an optionally substituted ($C_1$-$C_{12}$) alkynyl, an optionally substituted ($C_1$-$C_{11}$) hetero-alkynyl, an optionally substituted aryl, an optionally substituted ($C_3$-$C_{12}$) cycloalkyl, an optionally substituted ($C_3$-$C_{12}$) cycloalkenyl, and an optionally substituted heterocycle; and $R^9$ is selected from H, and a ($C_1$-$C_3$) alkyl.

2. The resorcinol-based compound of claim 1, wherein the resorcinol-based compound has a structure of:

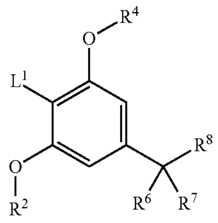

or a pharmaceutically acceptable salt, or prodrug thereof, wherein:

$L^1$ is selected from,

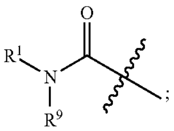
;

$R^1$ is selected from

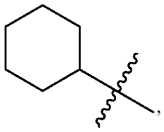
,
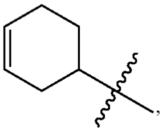
,
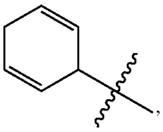
,
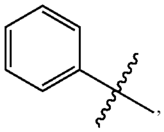
,
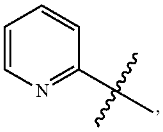
,
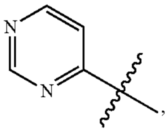
,
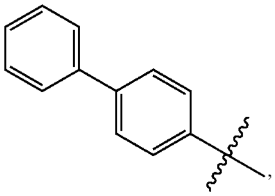
,
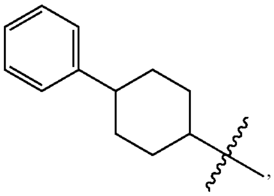
,
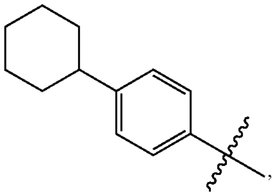
,
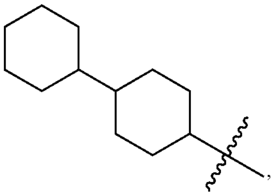
,
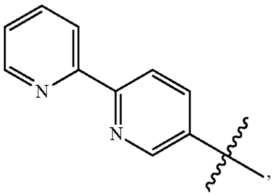
, -continued

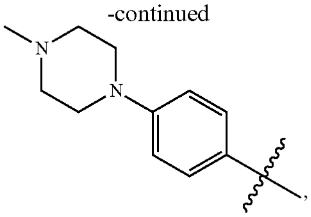
,
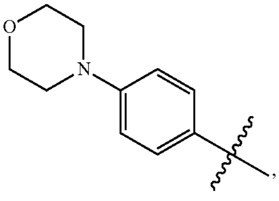
,
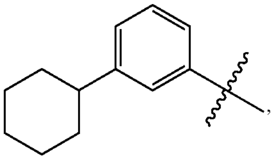
,
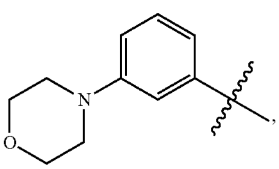
,
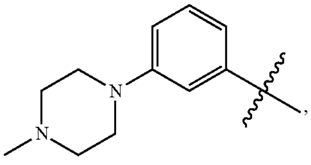
,
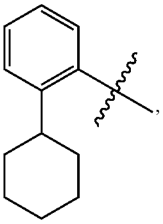
,
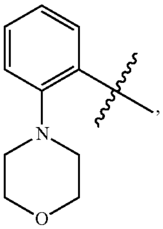
, and
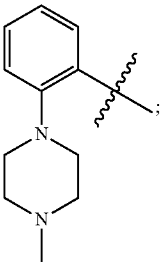
;

$R^2$, $R^4$, $R^6$, and $R^7$ are each independently selected from H or a methyl group;

$R^8$ is selected from an optionally substituted ($C_1$-$C_{12}$) alkyl, an optionally substituted ($C_1$-$C_{11}$) hetero-alkyl, an optionally substituted ($C_1$-$C_{12}$) alkenyl, an optionally substituted ($C_1$-$C_{11}$) hetero-alkenyl, an optionally substituted ($C_1$-$C_{12}$) alkynyl, an optionally substituted ($C_1$-$C_{11}$) hetero-alkynyl, an optionally substituted aryl, an optionally substituted ($C_3$-$C_{12}$) cycloalkyl, an optionally substituted ($C_3$-$C_{12}$) cycloalkenyl, and an optionally substituted heterocycle; and $R^9$ is selected from H, and a ($C_1$-$C_3$) alkyl.

3. The resorcinol-based compound of claim 1, wherein the resorcinol-based compound has a structure of Formula I (b):

I(b)

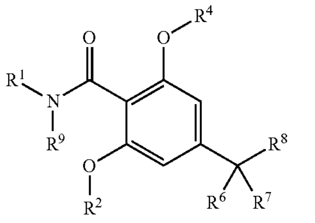

or a pharmaceutically acceptable salt, or prodrug thereof, wherein:

$R^1$ is selected from

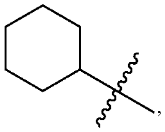
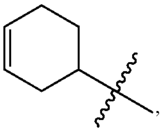
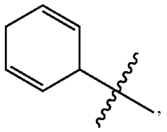
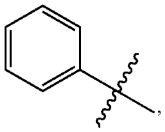
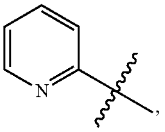
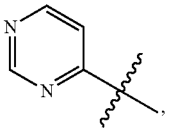
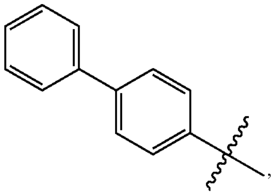
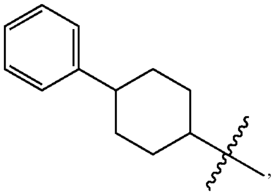
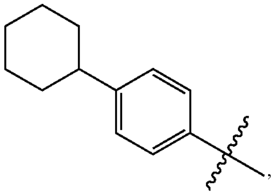
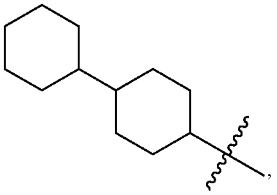
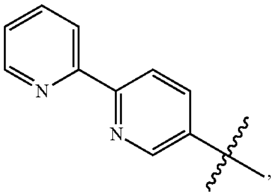
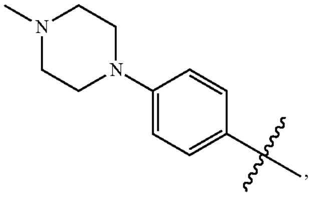

-continued

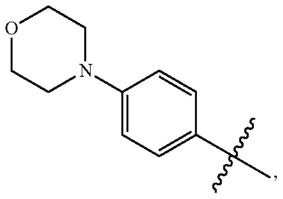
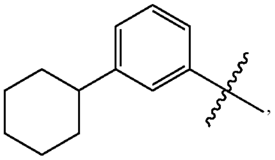
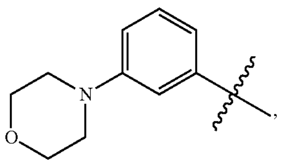
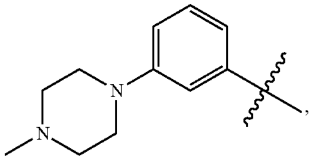
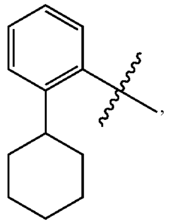
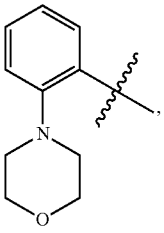

and

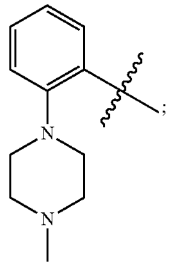

$R^2$, $R^4$, $R^6$, and $R^7$ are each independently selected from H or a methyl group;

$R^8$ is selected from a ($C_1$-$C_{12}$) alkyl, a ($C_2$-$C_{12}$) alkenyl, a ($C_2$-$C_{12}$) alkynyl, a ($C_3$-$C_8$) cycloalkyl, an aryl, a heterocycle, a —($CH_2$) x-aryl, a —$(CH_2)_x$-cycloalkyl, and a —$(CH_2)_x$-heterocycle, wherein X is an integer selected from 1, 2, 3, 4, 5, 6, 7, 8, 9, and 10; and $R^9$ is selected from H, and a ($C_1$-$C_3$) alkyl.

4. The resorcinol-based compound of claim 1, wherein the resorcinol-based compound has a structure selected from the group consisting of:

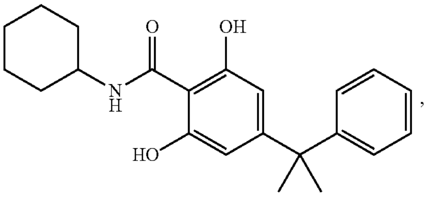

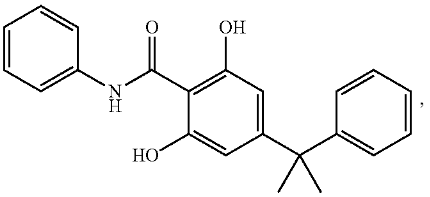

-continued

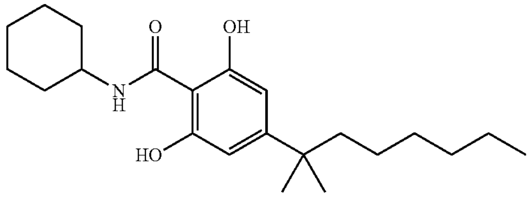

,

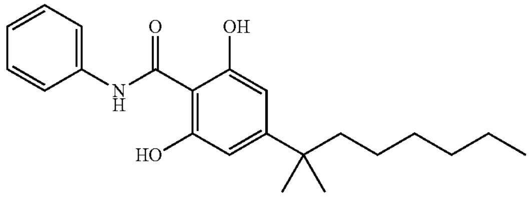

,

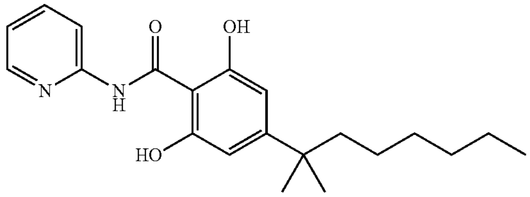

,

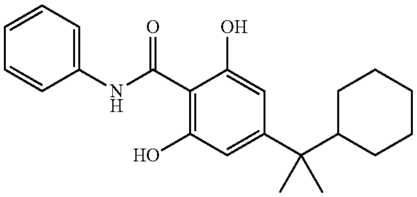

,

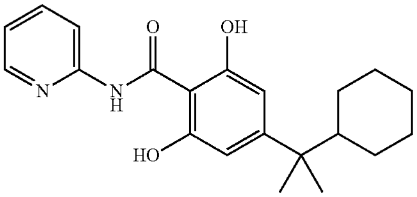

,

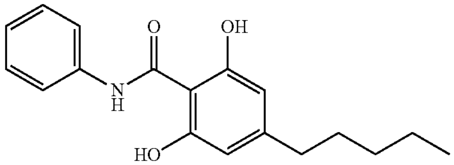

,

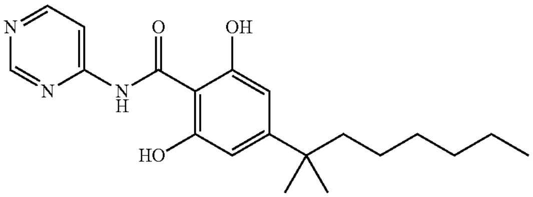

,

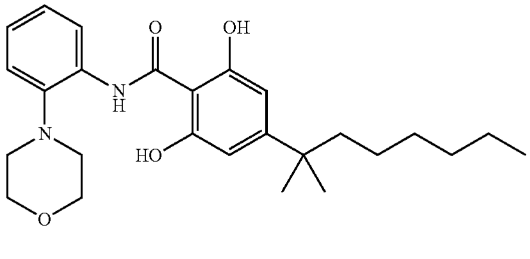

,

-continued

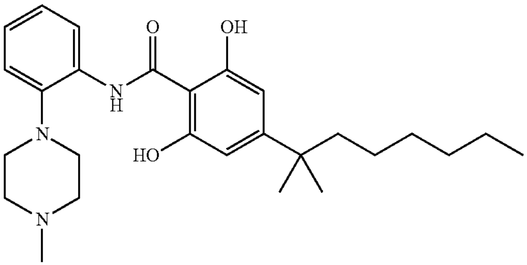

,

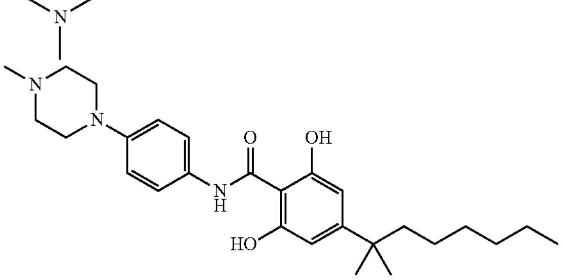

,

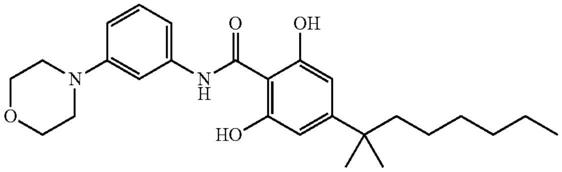

,

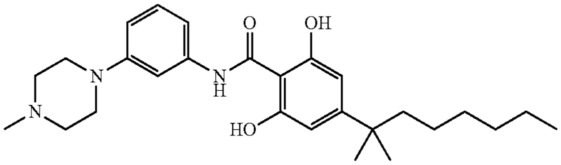

,

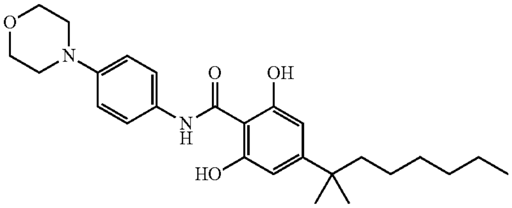

, and

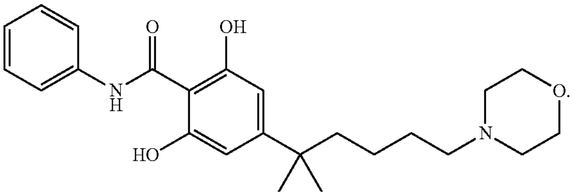

5. A pharmaceutical composition comprising the resorcinol-based compound of claim 1 and a pharmaceutically acceptable diluent, carrier and/or excipient.

6. The pharmaceutical composition of claim 5, wherein the pharmaceutical composition is formulated for oral or parenteral delivery.

7. The pharmaceutical composition of claim 5, wherein the pharmaceutical composition further comprises one or more additional therapeutic agents.

8. The pharmaceutical composition of claim 7, wherein the one or more additional therapeutic agents is selected from the group consisting of alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, and chemotherapeutic agents.

9. The pharmaceutical composition of claim 7, wherein the additional therapeutic agent is gemcitabine or 5-FU.

10. A method for regulating the expression of an inhibitor of DNA binding (Id), comprising contacting a cell that expresses the Id with an effective amount of a resorcinol-based compound of claim 1.

11. The method of claim 10, wherein the Id is Id-1.

12. A method for treating a cancer in a subject in need thereof, comprising: administering to the subject an effective amount of a resorcinol-based compound of claim 1.

13. The method of claim 12, wherein the cancer is a metastatic cancer.

14. The method of claim 12, wherein the cancer is selected from the group consisting of pancreatic cancer, breast cancer, ovarian cancer, prostate cancer, non-small cell lung cancer, gastric cancer, melanoma, glioblastoma, hepatocarcinoma, blood cancers, and anaplastic thyroid tumor.

15. The method of claim 14, wherein the cancer is pancreatic cancer.

16. A method for inhibiting cancer cell invasiveness and metastatic progression in a subject in need thereof, comprising: administering to the subject an effective amount of a resorcinol-based compound of claim 1.

17. The method of claim 16, wherein the cancer cell invasiveness and metastatic progression is inhibited by downregulating Id-1 expression.

18. The method of claim 16, wherein the subject has a cancer selected from the group consisting of pancreatic cancer, breast cancer, prostate cancer, non-small cell lung cancer, gastric cancer, melanoma, glioblastoma, hepatocarcinoma, and anaplastic thyroid tumor.

19. The method of claim 18, wherein the subject has pancreatic cancer.

* * * * *